(12) United States Patent
Davagian

(10) Patent No.: US 10,525,242 B2
(45) Date of Patent: Jan. 7, 2020

(54) METHOD AND APPARATUS FOR INSERTING A RECTAL SUPPOSITORY

(71) Applicant: Cristcot LLC, Concord, MA (US)

(72) Inventor: Jennifer J. Davagian, Sudbury, MA (US)

(73) Assignee: Cristcot LLC, Concord, MA (US)

( * ) Notice: Subject to any disclaimer, the term of this patent is extended or adjusted under 35 U.S.C. 154(b) by 0 days.

(21) Appl. No.: 15/498,229

(22) Filed: Apr. 26, 2017

(65) Prior Publication Data

US 2017/0224971 A1 Aug. 10, 2017

Related U.S. Application Data

(60) Division of application No. 13/840,096, filed on Mar. 15, 2013, now Pat. No. 9,662,481, which is a continuation-in-part of application No. 13/456,875, filed on Apr. 26, 2012, now Pat. No. 8,419,712, which is a division of application No. 12/287,215, filed on Oct. 7, 2008, now Pat. No. 8,192,393.

(51) Int. Cl.
*A61M 31/00* (2006.01)

(52) U.S. Cl.
CPC .................. *A61M 31/007* (2013.01)

(58) Field of Classification Search
CPC .................................................. A61M 31/007
See application file for complete search history.

(56) References Cited

U.S. PATENT DOCUMENTS 330,764 A 11/1885 Worley
504,512 A 9/1893 Bailey
(Continued)

FOREIGN PATENT DOCUMENTS

CN 2416896 Y 1/2001
CN 201586319 U 9/2010
(Continued)

OTHER PUBLICATIONS

Banerjee, S., et al., "Inflammatory Bowel Disease Medical Therapy of Specific Clinical Presentations," *Gastroenterol Clin N Am*, 31: 185-202 (2002).
(Continued)

*Primary Examiner* — Imani N Hayman
(74) *Attorney, Agent, or Firm* — Hamilton, Brook, Smith & Reynolds, P.C.

(57) ABSTRACT

Rectal suppositories are used to administer a predetermined drug dosage to treat a variety of diseases and symptoms in a variety of patient populations. Certain medical conditions, such as digestive disorders, may be more effectively treated when the suppository is placed in a particular location of the patient's anal canal or rectum. An apparatus for inserting a suppository can include an applicator having a barrel, such as a hollow cylindrical body, and a plunger, such as a substantially cylindrical elongated body. The apparatus can include features to ensure that beneficial gas flow paths associated with the plunger or the barrel are maintained or that the apparatus can accommodate suppositories of different sizes. Embodiments may include features to facilitate gripping and manipulation of the apparatus for use by patients with limited dexterity. These benefits may encourage patients to maintain a course of treatment, thereby potentially avoiding additional complications, hospitalization, and costs.

15 Claims, 23 Drawing Sheets

(56) References Cited

U.S. PATENT DOCUMENTS

| | | |
|---|---|---|
| 2,281,600 A | 5/1942 | Ross |
| 2,290,571 A | 7/1942 | Peyton |
| 2,443,207 A | 6/1948 | Tedford |
| 2,503,445 A | 4/1950 | Lermer |
| 2,532,598 A | 12/1950 | Boeger |
| 2,680,442 A | 6/1954 | Linzmayer |
| 2,709,436 A | 5/1955 | Lynn |
| 2,754,823 A | 7/1956 | Miller |
| 3,015,332 A | 1/1962 | Brecht |
| 3,139,886 A | 7/1964 | Tallman et al. |
| 3,220,413 A | 11/1965 | Sunnen |
| 3,667,465 A | 6/1972 | Voss |
| 3,780,735 A | 12/1973 | Crouter et al. |
| 3,835,856 A | 9/1974 | Warncke |
| 3,840,010 A | 10/1974 | Giglio |
| 4,248,229 A | 2/1981 | Miller |
| 4,341,211 A | 7/1982 | Kline |
| 4,341,221 A | 7/1982 | Testerman |
| 4,361,150 A | 11/1982 | Voss |
| 4,406,655 A | 9/1983 | Clayton |
| 4,421,504 A | 12/1983 | Kline |
| 4,752,288 A | 6/1988 | Hussey |
| 4,990,136 A | 2/1991 | Geria |
| 5,152,068 A | 10/1992 | Meister et al. |
| D330,764 S | 11/1992 | Lorentzon |
| 5,160,689 A | 11/1992 | Kamen |
| 5,213,566 A | 5/1993 | Weissenburger |
| 5,330,427 A | 7/1994 | Weissenburger |
| 5,352,681 A | 10/1994 | Wittebrood et al. |
| 5,354,325 A | 10/1994 | Chive et al. |
| 5,460,617 A | 10/1995 | Minkus et al. |
| 5,656,283 A | 8/1997 | Brummer et al. |
| 5,662,601 A | 9/1997 | Snead |
| 5,788,664 A | 8/1998 | Scalise |
| 5,860,946 A | 1/1999 | Hofstätter |
| 6,056,714 A | 5/2000 | McNelis et al. |
| D436,661 S | 1/2001 | Berry |
| 6,190,348 B1 | 2/2001 | Tiemann et al. |
| 6,245,776 B1 | 6/2001 | Skwierczynski et al. |
| 6,380,455 B1 | 4/2002 | Moder et al. |
| 6,486,168 B1 | 11/2002 | Skwierczynski et al. |
| 6,500,460 B1 | 12/2002 | Bergeron et al. |
| D471,980 S | 3/2003 | Caizza |
| 6,706,728 B2 | 3/2004 | Hedenstrom et al. |
| 6,740,333 B2 | 5/2004 | Beckett et al. |
| 6,786,883 B2 | 9/2004 | Shippert |
| 6,916,308 B2 | 7/2005 | Dixon et al. |
| 7,070,581 B2 | 7/2006 | Manera et al. |
| 7,081,110 B2 | 7/2006 | Karapasha |
| 7,104,968 B2 | 9/2006 | Swick |
| D529,603 S | 10/2006 | Knickerbocker et al. |
| 7,122,025 B1 | 10/2006 | Nestenborg |
| 7,149,574 B2 | 12/2006 | Yun et al. |
| 7,192,607 B2 | 3/2007 | Bergeron et al. |
| 7,198,612 B2 | 4/2007 | Swick |
| 7,217,252 B2 | 5/2007 | Swick |
| 7,361,168 B2 | 4/2008 | Makower et al. |
| D572,362 S | 7/2008 | Edgett et al. |
| D579,786 S | 11/2008 | Py et al. |
| 7,465,295 B2 | 12/2008 | Bergeron et al. |
| D585,988 S | 2/2009 | Kinnard |
| 7,503,895 B2 | 3/2009 | Rabiner et al. |
| 7,591,808 B2 | 9/2009 | DiPiano et al. |
| D608,659 S | 1/2010 | Py et al. |
| 7,666,160 B2 | 2/2010 | Rajala et al. |
| 8,192,393 B2 | 6/2012 | Ensign |
| 8,419,712 B2 | 4/2013 | Ensign |
| 9,662,481 B2 | 5/2017 | Davagian |
| 10,149,967 B2 | 12/2018 | Davagian et al. |
| 2002/0048601 A1 | 4/2002 | Beckett et al. |
| 2002/0058674 A1 | 5/2002 | Hedenstrom et al. |
| 2003/0045543 A1 | 3/2003 | Hedenstrom et al. |
| 2003/0088217 A1 | 5/2003 | Bergeron et al. |
| 2003/0233077 A1 | 12/2003 | Swick |
| 2003/0233078 A1 | 12/2003 | Swick |
| 2004/0047910 A1 | 3/2004 | Beckett et al. |
| 2004/0249352 A1 | 12/2004 | Swick |
| 2004/0249416 A1 | 12/2004 | Yun et al. |
| 2004/0260252 A1 | 12/2004 | DiPiano et al. |
| 2005/0004533 A1 | 1/2005 | Smith |
| 2005/0021092 A1 | 1/2005 | Yun et al. |
| 2005/0143378 A1 | 6/2005 | Yun et al. |
| 2005/0143788 A1 | 6/2005 | Yun et al. |
| 2005/0153885 A1 | 7/2005 | Yun et al. |
| 2005/0240241 A1 | 10/2005 | Yun et al. |
| 2005/0256028 A1 | 11/2005 | Yun et al. |
| 2005/0273038 A1 | 12/2005 | Osborn, III et al. |
| 2006/0034847 A1 | 2/2006 | Yun et al. |
| 2006/0035974 A1 | 2/2006 | Yun et al. |
| 2006/0069012 A1 | 3/2006 | Yun et al. |
| 2006/0184100 A1 | 8/2006 | Studin |
| 2006/0206149 A1 | 9/2006 | Yun |
| 2007/0073267 A1 | 3/2007 | Muller |
| 2007/0112327 A1 | 5/2007 | Yun et al. |
| 2007/0129668 A1 | 6/2007 | Swick |
| 2007/0185436 A1 | 8/2007 | Swick |
| 2008/0038377 A1 | 2/2008 | Citow |
| 2008/0097286 A1 | 4/2008 | Cleator et al. |
| 2008/0161752 A1 | 7/2008 | Rajala et al. |
| 2008/0167598 A1 | 7/2008 | Gann et al. |
| 2008/0167599 A1 | 7/2008 | Osborn et al. |
| 2008/0300575 A1 | 12/2008 | Cleator et al. |
| 2008/0319269 A1 | 12/2008 | Longo et al. |
| 2010/0010471 A1 | 1/2010 | Ladd et al. |
| 2010/0145379 A1 | 6/2010 | Isham |
| 2015/0265820 A1 | 9/2015 | Ensign et al. |
| 2017/0224971 A1 | 8/2017 | Davagian |
| 2019/0143088 A1 | 5/2019 | Davagian |
| 2019/0151636 A1 | 5/2019 | Davagian et al. |

FOREIGN PATENT DOCUMENTS

| | | |
|---|---|---|
| DE | 3031408 A1 | 3/1982 |
| EP | 1 040 808 A2 | 10/2000 |
| EP | 1 319 420 A1 | 6/2003 |
| EP | 1 530 978 A1 | 5/2005 |
| FR | 1190750 A | 10/1959 |
| FR | 2 923 999 A1 | 5/2009 |
| JP | S59-181834 U | 10/1984 |
| JP | H05-070545 U | 9/1993 |
| JP | H05-279243 A | 10/1993 |
| JP | H09-103467 A | 4/1997 |
| JP | 2001-070456 A | 3/2001 |
| JP | 2007-215732 A | 8/2007 |
| JP | 2012-5719 A | 1/2012 |
| WO | WO 01/91605 | 12/2001 |
| WO | 2004/112755 A1 | 12/2004 |
| WO | WO 2004/112755 A1 | 12/2004 |
| WO | WO 03/101525 A1 | 12/2005 |
| WO | WO 2006/063377 A1 | 6/2006 |
| WO | WO 2006/077617 A1 | 7/2006 |
| WO | WO 2008/081353 A1 | 7/2008 |
| WO | WO 2008/084453 A1 | 7/2008 |
| WO | WO 2008/102341 A2 | 8/2008 |
| WO | 2010/042468 A2 | 4/2010 |
| WO | WO 2010/042468 A2 | 4/2010 |
| WO | WO 2014/063122 A1 | 4/2014 |
| WO | 2017197100 | 11/2017 |

OTHER PUBLICATIONS

Bradshaw, A., "Rectal Suppository Insertion: The Reliability of the Evidence as a Basis for Nursing Practice," *Journal of Clinical Nursing*, 16: 98-103 (2006).

Fernandez-Becker, N. Q., et al., "Improving Delivery of Aminosalicylates in Ulcerative Colitis," *Drugs*, 68(8): 1089-1103 (2008).

Hidaka, N., et al., "Changes in the Plasma Diazepam Concentration and Its Anticonvulsant Effect After the Discharge of a Diazepam Suppository from the Rectum in Rats," *Methods Find Exp Clin Pharmacol*, 29(6): 401-404 (2007).

Howell, H. R., "Ulcerative Colitis: Achieving and Maintaining Remission," *US Pharm*, 33(12): 30-37 (2008).

(56) References Cited

OTHER PUBLICATIONS

Regueiro, M., et al., "Medical Management of Left-Sided Ulcerative Colitis and Ulcerative Proctitis: Critical Evaluation of Therapeutic Trials," *Inflamm Bowel Dis*, 12(10): 979-994 (2006).

Tindall, W. N., et al., "Mild-to-Moderate Ulcerative Colitis: Your Role in Patient Compliance and Health Care Costs," *Supplement to Journal of Managed Care Pharmacy*, 13(7, S-a): S2-S15 (2007) (with attached 2-page Evaluation).

Expedited Review Request, Letter and Attachments A-C from Jennifer Davagian Ensign regarding Expedited Review of 510(k) Premarket Notification, dated Sep. 4, 2009.

International Search Report and Written Opinion of the International Searching Authority from International Application No. PCT/US2009/059623 "Method and Apparatus for Inserting a Rectal Suppository," dated Jun. 16, 2010.

Amendment under Article 34 and Reply to Written Opinion filed in International Application No. PCT/US2009/059623 "Method and Apparatus for Inserting a Rectal Suppository," dated Sep. 16, 2010.

International Preliminary Report on Patentability from International Application No. PCT/US2009/059623 "Method and Apparatus for Inserting a Rectal Suppository," dated Mar. 28, 2011.

International Search Report and the Written Opinion of the International Searching Authority from Application No. PCT/US2013/065795, dated Feb. 7, 2014, "Suppository Insertion Device, Suppository, and Method of Manufacturing a Suppository".

International Preliminary Report on Patentability/Written Opinion of the International Searching Authority for International Application No. PCT/US2013/065795, dated Apr. 21, 2015, entitled "Suppository Insertion Device, Suppository, and Method of Manufacturing a Suppository".

International Search Report and Written Opinion for PCT/US22017/032142, dated Aug. 29, 2017, entitled "Single-Use Suppository Insertion Device and Method," 14 pages.

Partial European Search Report for Application No. 17168072.1-1653, dated Oct. 4, 2017, entitled "Suppository Insertion Device, Suppository, and Method of Manufacturing a Suppository," 12 pages.

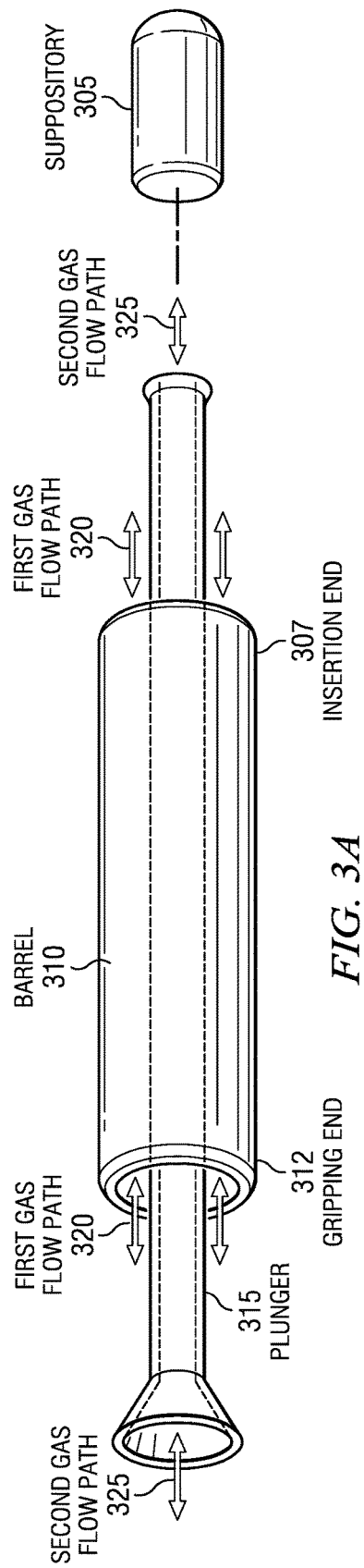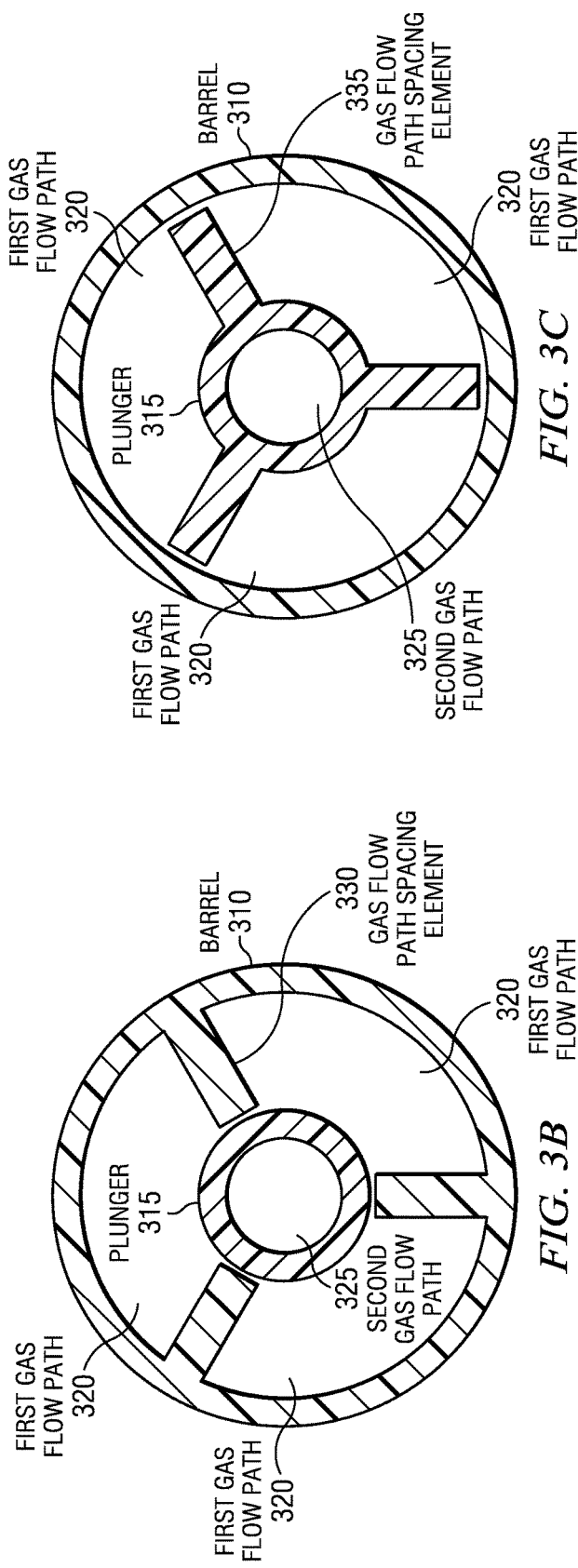

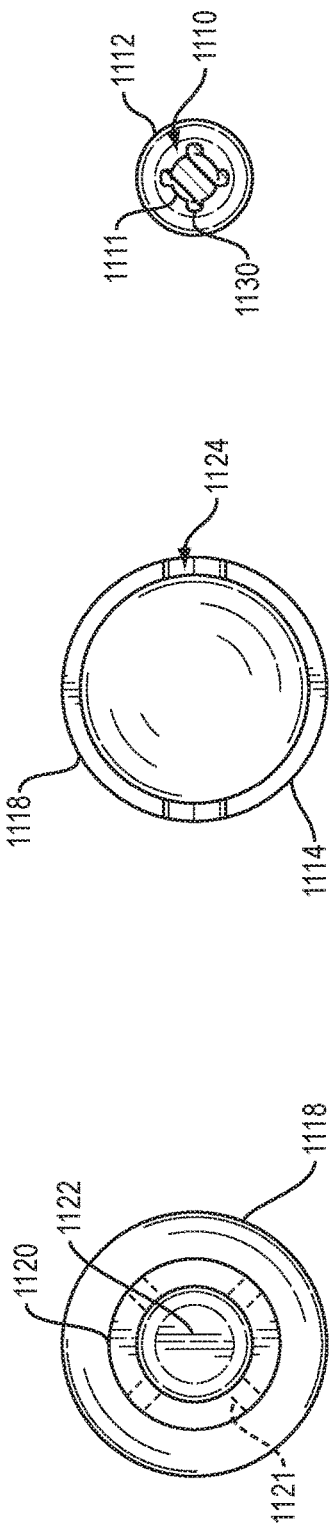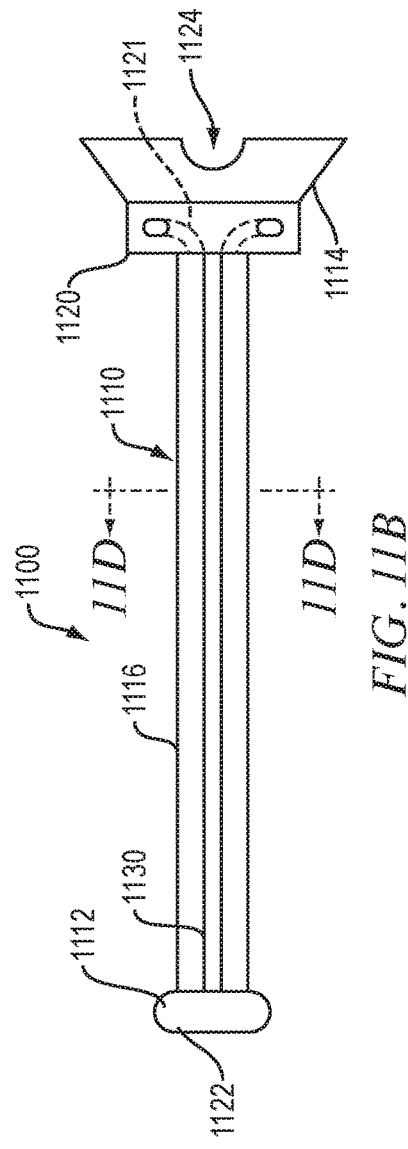

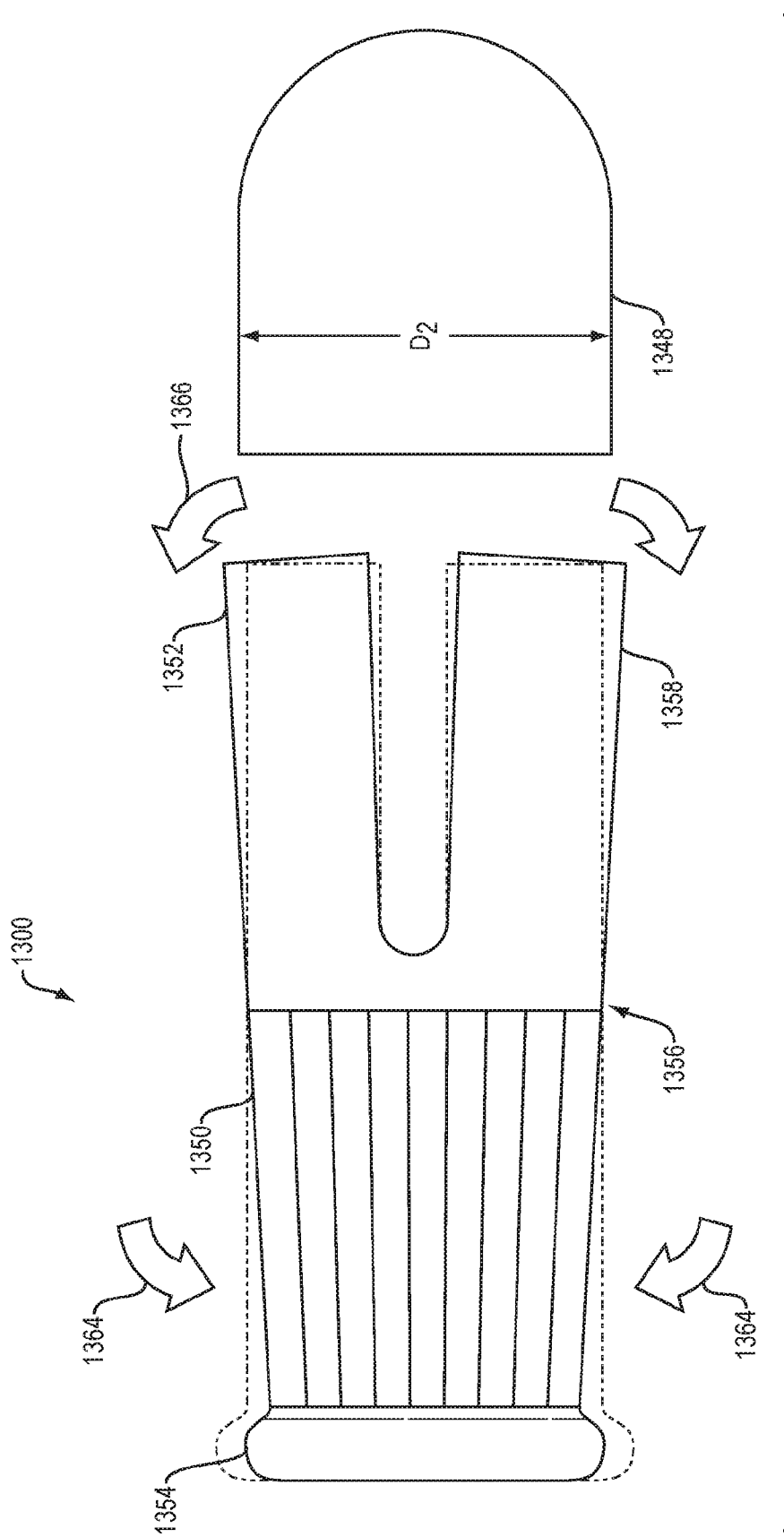

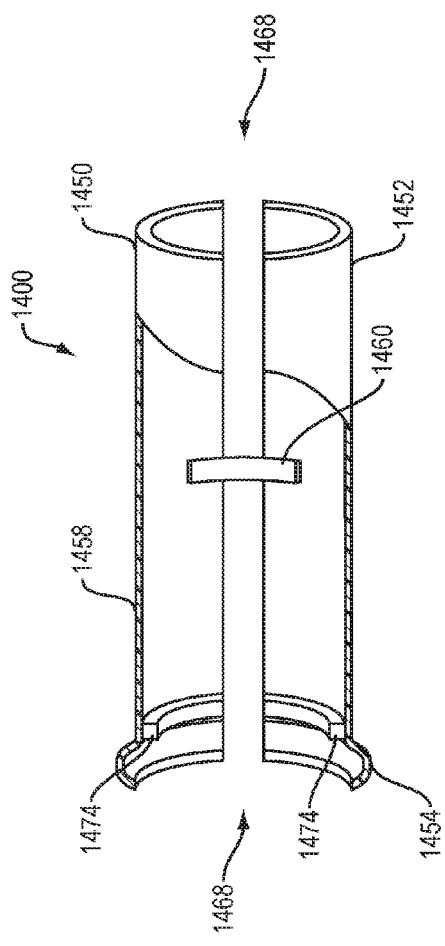
FIG. 14B
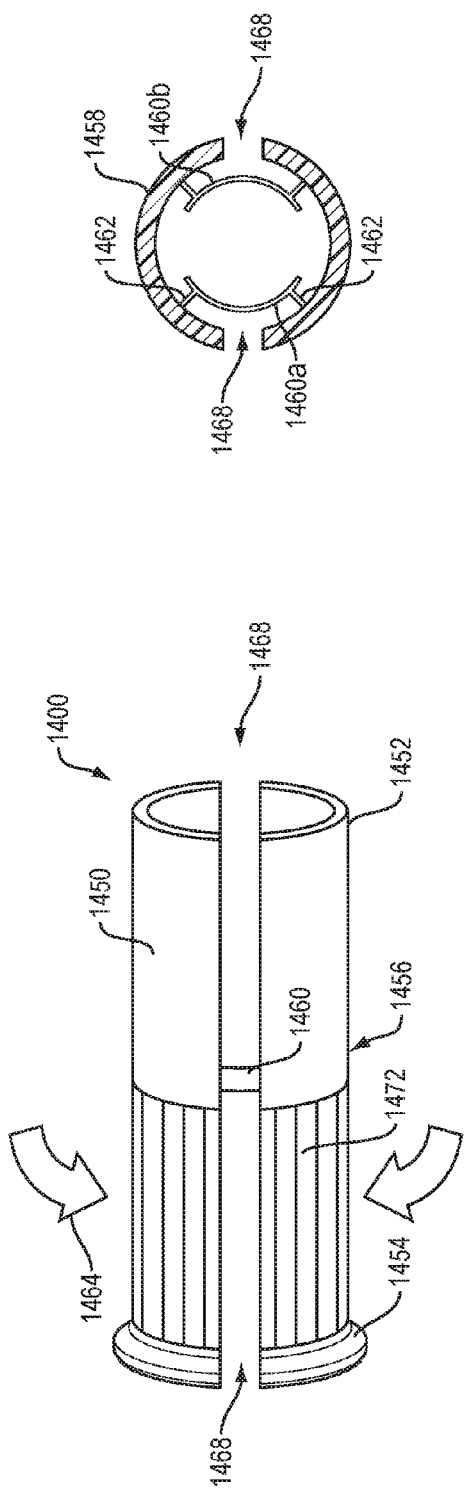
FIG. 14A
FIG. 14C

METHOD AND APPARATUS FOR INSERTING A RECTAL SUPPOSITORY

RELATED APPLICATIONS

This application is a divisional of U.S. application Ser. No. 13/840,096, filed Mar. 15, 2013, which is a continuation-in-part of U.S. application Ser. No. 13/456,875, filed Apr. 26, 2012, now U.S. Pat. No. 8,419,712, which is a divisional of U.S. application Ser. No. 12/287,215, filed Oct. 7, 2008, now U.S. Pat. No. 8,192,393. The entire teachings of the above applications are incorporated herein by reference.

BACKGROUND OF THE INVENTION

Rectal suppositories are used to administer a predetermined drug dosage to treat a variety of diseases and symptoms. Rectal suppositories are designed to melt inside the body allowing the drug dosage contained within the rectal suppository to be absorbed by the mucosa lining of the rectum in order to treat a patient locally or systemically. Suppositories are typically used to administer drugs to patients who cannot take the drug orally for a variety of reasons, such as uncontrollable vomiting or nausea, chronic illnesses, and gastrointestinal diseases. In addition, children, the elderly, and patients unable to care for themselves may also use rectal suppositories to treat a variety of symptoms and conditions. In other cases, specific drugs can cause extreme stomach upset or are inactivated in the stomach or liver and are, therefore, better tolerated by rectal administration.

It is common practice to administer rectal suppositories manually using a finger while the patient is, for example, lying on their left side in the fetal position, and after having emptied their bowel. After insertion of the suppository, the patient is instructed to remain on their side in the fetal position for an extended period of time (e.g., at least 30 minutes) while the suppository has time to melt within the rectum and the body begins the absorption process.

SUMMARY OF THE INVENTION

An apparatus and corresponding method for inserting a rectal suppository into an animal or human according to example embodiments includes a barrel configured to be inserted into an anal canal, the barrel having ends defining at least one first gas flow path into and out of the body. The example embodiment further includes a plunger defining at least one second gas flow path into and out of the body and is configured to be movably coupled to the barrel with the at least one first gas flow path maintained. The plunger is movably extendable past an open end of the barrel to insert a suppository into the rectum while maintaining the at least one first gas flow path during a state of insertion of the suppository into the rectum. The at least one second gas flow path is maintained during withdrawal of the plunger away from the suppository.

Alternative example embodiments may further include an insertion end of the plunger that is configured to insert the suppository above an "anal trigger zone" into the rectum to minimize contact of the suppository or its medication with nerves that trigger contraction of anal sphincter muscles that may affect the body's ability to retain and absorb the medication.

Other example embodiments may further include at least one gas flow path spacing element configured to maintain the at least one first gas flow path with the plunger movably coupled to the barrel. The barrel may include the at least one gas flow path spacing element, the at least one gas flow path spacing element extending inward from an inner wall of the barrel while maintaining the at least one first gas flow path defined by the barrel to contact an outer wall of the plunger. Alternatively, the plunger may include the at least one gas flow path spacing element, the at least one gas flow path spacing element extending outward from an outer wall of the plunger while maintaining the at least one first gas flow path defined by the barrel to contact an inner wall of the barrel.

In another example embodiment, the barrel can include at least one gas flow path spacing element extending inward while maintaining the at least one first gas flow path defined by the barrel and wherein the plunger includes at least one gas flow path spacing element extending outward while maintaining the at least one first gas flow path. Alternatively, the embodiment may include at least two gas flow path spacing elements, defined by at least one gas flow path spacing element extending inward from the barrel and at least one gas flow path spacing element extending outward from the plunger, wherein the at least two gas flow path spacing elements are configured to interconnect in a movable relationship to each other.

According to other example embodiments, the barrel and the plunger may be shaped to provide at least one gas flow path between each other with the plunger positioned at least partially within the barrel. The barrel may include at least two subbarrels arrangeable to form the barrel and the plunger may include at least two subplungers arrangeable to form the plunger.

In yet another example embodiment, the barrel and the plunger each defines a hollow tube. The barrel may include an inner wall that defines a hollow tube and further includes an outer wall coupled to the inner wall by a structure to define the at least one first gas flow path. Conversely, the plunger may define a non-hollow structure and at least one gas flow path spacing element extending outward from a wall of the structure is configured to press on tissue between the anal canal or rectum and the plunger in a manner defining the at least one second gas flow path.

Some example embodiments may include a suppository support element configured to support a suppository at least partially below an open end of the barrel. The plunger may include a suppository interface end that is as wide or wider than a portion of the suppository with which the interface end is configured to contact. Alternatively, the plunger includes a suppository interface end that is narrower than a portion of the suppository with which the interface end is configured to contact.

In accordance with another example embodiment, the plunger has an insertion end and a hand or finger-interface end where the plunger has a length that enables a user self-administering the suppository to push the plunger with their palm or finger tip against the hand or finger-interface end. Note that the barrel or plunger may be formed from plastic, polycarbonate, epoxy, acrylic, silicon, rubber, polymer, ceramic, metal, cardboard, glass, wood, paper, or similar such materials.

Alternative example embodiments for inserting a suppository into an animal or human may include a barrel configured to insert into an anal canal and a plunger defining at least one gas flow path and is further configured to be coupled to the barrel with the at least one gas flow path maintained. The plunger is extendable past an open end of the barrel to insert a suppository into the anal canal or rectum while maintaining the at least one gas flow path during a state of withdrawal of the plunger away from the suppository. The plunger may be fixedly coupled to the barrel. Alternatively, the plunger may be movably coupled to the barrel. The plunger may be further configured to insert the suppository into the rectum.

In another example embodiment, an apparatus for inserting a suppository into an animal or human includes a substantially cylindrical elongated body having an insertion end, a hand or finger-interface end, and a central portion extending between the insertion end and the hand or finger-interface end. The insertion end has a larger diameter than the central portion. The interface end includes an interface portion to interface with a hand or finger. The interface end further includes a stepped portion that is wider than the central portion and positioned between the central portion and the interface portion.

The body of the apparatus can define a hollow structure, such as a hollow tube or hollow plunger. The hollow structure may be configured to maintain a gas flow path. Alternatively, the body of the apparatus may define a non-hollow structure, such as a solid rod or plunger, and may further define at least one spacing element extending outward from a wall of the structure. The spacing element may be a gas flow path spacing element that extends outward from the wall of the structure and is configured to press on tissue between an anal canal or rectum and the apparatus in a manner defining at least one gas flow path.

In the example embodiment, the insertion end can include a suppository interface portion. The suppository interface portion may be as wide as or wider than a portion of a suppository with which the interface portion is configured to contact. Alternatively, the suppository interface portion may be narrower than a portion of a suppository with which the interface portion is configured to contact.

In an embodiment, the stepped portion does not extend around the entire circumference of the body. Alternatively, the stepped portion can extend around the entire circumference. Further, the stepped portion may define a gas (e.g., air) pathway therethrough. The interface portion of the hand or finger-interface end may be cup-shaped to accept a tip of a finger. Further, there can be at least one opening, groove, or notch in a sidewall of the interface portion to allow for gas flow when a finger is in contact with the interface portion.

In another example embodiment, an apparatus for inserting a suppository into an animal or human includes a hollow cylindrical body having an insertion end, a gripping end, and a central portion. The central portion includes an outer wall and an inner structure coupled to the outer wall by an attachment. The body of the apparatus can be mechanically arranged to enable squeezing or compressing of the central portion, e.g., between the gripping end and the attachment, whereby squeezing of the central portion, e.g., at the gripping end behind the attachment, causes outward movement of the outer wall at the insertion end in front of the attachment.

The mechanical arrangement may include a longitudinal slot, cut, or opening in the outer wall. Alternatively or in addition, the mechanical arrangement can include a portion of the outer wall being structurally compliant enough to expand in response to insertion of a suppository into the insertion end. The mechanical arrangement can be configured to accommodate suppositories of different diameters. The apparatus may further include a suppository support element configured to support a suppository at least partially inside an open end, e.g., the open insertion end, of the body of the apparatus.

The outer wall can include ridges that extend from the gripping end along a length of the body. The gripping end can have a larger diameter than the central portion. Such features of the outer wall or the gripping end facilitate manipulation of the apparatus by a patient.

In any of the example embodiments, the apparatus, or portions thereof, may be formed from plastic, polycarbonate, epoxy, acrylic, silicone, rubber, polymer, ceramic, metal, cardboard, glass, wood, paper, or similar such materials.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A-C are illustrations of applicators configured to insert a rectal suppository according to example embodiments of the invention;

FIGS. 11A-D are respective front, side, back, and sectional views of another example embodiment of the invention;

FIGS. 13A-B are illustrations of an alternative embodiment of the invention that can accommodate suppositories of various sizes; and FIG. 14A-C are illustrations of yet another embodiment of the invention that can accommodate suppositories of various sizes.

DETAILED DESCRIPTION OF THE INVENTION

A description of example embodiments of the invention follows.

The effect of many drugs administered orally may be reduced or inactivated in the stomach because of the acidic and/or enzymatic content of the stomach or the drug may be subject to digestive attack and/or to microbial degradation. Oral administration of drugs also directs the absorbed substances through the liver where the drug's effectiveness can be further reduced or inactivated. As a result, rectal suppositories are often the most effective mode of delivery for the administration of a variety of drugs associated with medical conditions.

Rectal suppositories are composed of active pharmacological ingredients and an inactive binding agent that maintains the drug in a desired shape and stable form prior to, and during, insertion into the rectum. The inactive binding agents are designed so that the suppositories remain stable at or below room temperature. At or above body temperature, suppositories are designed to melt or dissolve so that the encapsulated medication may be released for absorption by the patient. Suppositories are formed to ease insertion and are commonly manufactured to maintain a round or bullet shaped appearance.

Drugs administered via rectal suppositories are intended to obtain a local therapeutic effect or systemic therapeutic effect. The effective ingredient in the medicine administrated by rectal application is often intended to be directly absorbed in the venous plexus of the rectum to be distributed throughout the body by the blood circulation without passing the portal vein and the liver. Therefore, a rectally applicable medicament form is preferable particularly for the medicines for which the effective ingredient causes a disorder in the stomach when orally administered or the ingredient is susceptible to decomposition in the digestive tract or liver resulting in decreased effectiveness of the medicine.

The effectiveness and convenience of a number of drugs administered via rectal suppository form can be improved if positioned in a particular region of the anal canal or rectum. For example, rectal suppositories used for the treatment of hemorrhoids may be positioned relatively shallow. On the other hand, certain types of drugs, such as those used for digestive disorders, may be inserted relatively deeper, that is, further up the anal canal or into the rectum, to ensure sufficient absorption, to treat a greater portion of the gastrointestinal tract, and to prevent leakage of the drug out of the body.

Figure 1A:
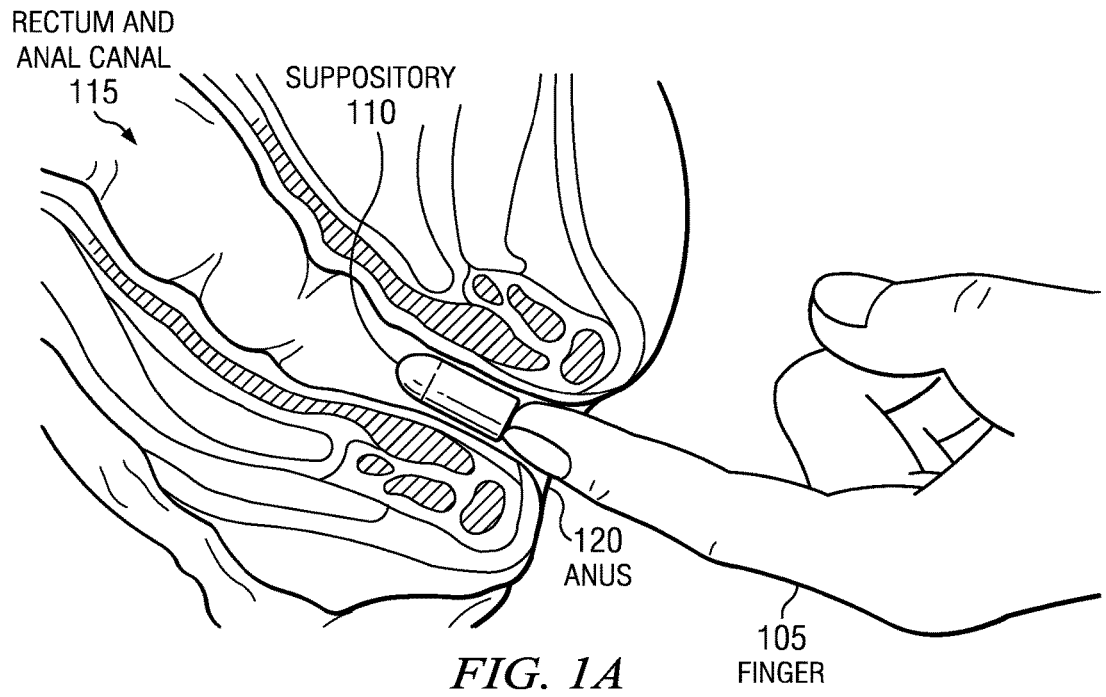
FIGS. 1A-B illustrate known techniques for inserting a rectal suppository.

FIG. 1A illustrates a known technique for inserting a suppository 110 by using a finger 105 to manually insert the suppository into a body cavity, such as a rectum or anal canal 115. To use this technique, it is necessary to wash hands thoroughly prior to insertion, or alternatively, enclose the finger 105 or hand with a sanitized latex covering or the like. The patient or medical personnel aligns one end the suppository 110 with the patient's anus 120. After the suppository 110 is properly aligned, the finger 105 is used to push the suppository 110 into an optimal position in the rectum or anal canal 115 and the finger 105 is removed. Once in place, the patient's body heat will begin to melt the suppository 110 releasing the encapsulated medication so that the drug can began to be absorbed within the patient's rectum or anal canal 115.

However, when used with rectal suppositories, the finger insertion technique suffers from a number of disadvantages that significantly impact convenience and drug absorption. First, when the finger 105 is withdrawn from the rectum or anal canal 115, a pocket of air is created and remains in the rectum or anal canal 115 as trapped gas. The trapped gas will eventually be released as flatulence. Along with the passage of gas, a portion of the suppository 110 that has melted due to body temperature, but not yet absorbed by the mucosa lining of the rectum, is expelled from the body, staining the patient's clothing. To prevent ruining clothing and embarrassing accidents, many patients resort to wearing sanitary pads and undergarments. The released gas may also be embarrassing for the patient in social situations. Second, withdrawal of the finger 105 also creates a suction effect that draws the suppository 110 out of the intended position, moving the suppository 110 toward the opening of the rectum or anal canal 115. This movement further increases the likelihood of drug leakage and/or expulsion. Third, certain drugs, such as those for digestive disorders, have an optimal placement position deeper than that which is obtainable using this or other known techniques due to, for example, limited finger 105 length or body mechanics in the case of self administration. Because the suppository 110 is placed in a shallower position than optimal, the potential for leakage and/or expulsion is further increased thereby reducing the amount of medication that is absorbed by the body. In addition, shallow placement may also stimulate internal sphincter muscles creating a sensation in the patient indicative of a need to empty their bowel. Fourth, the inner wall of the rectum or anal canal 115 is easily scratched and injured by the finger's 105 fingernail resulting in potential injury and/or pain. If used with a latex glove or finger wrap, the latex may tear and can cause irritation in some patients.

Figure 1B:
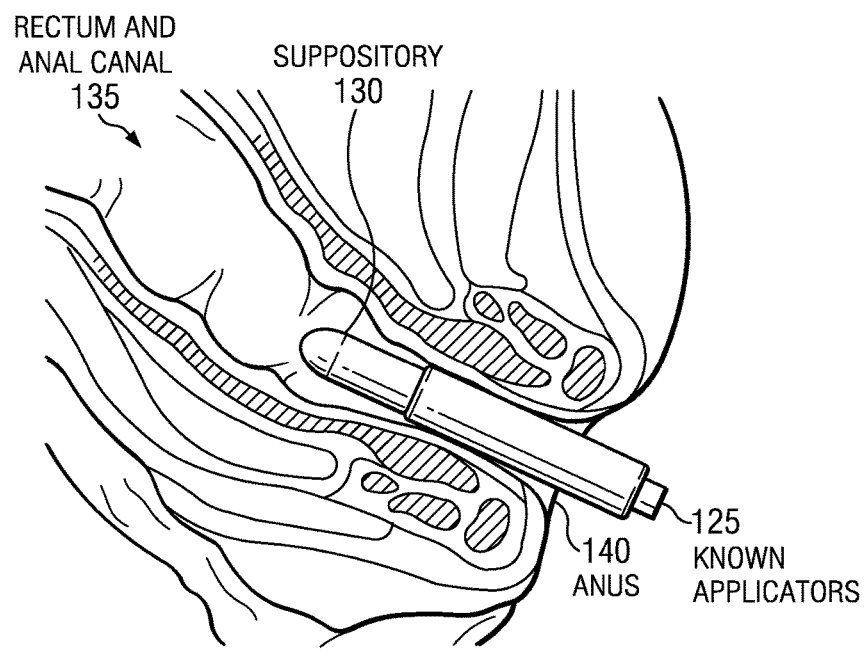

FIG. 1B illustrates another technique for inserting a rectal suppository 130 include the use of various known applicators 125. Such applicators 125 are more hygienic and can aid in the ergonomic difficulties of self administration. These applicators 125 are typically modified versions of vaginal applicators used for shallow placement of objects, such as tampons or medicated creams, into the vaginal canal. As such, these applicators 125 are designed to accommodate anatomical features of the vagina rather than the anal canal and rectum 135. The smooth, flat muscles of the vagina walls do not subconsciously and spontaneously contract. Furthermore, vaginal-type applicators 125 are not intended to insert objects beyond the relatively shallow depth of the vagina. Consequently, due to the anatomical characteristics of the vagina, vaginal applicators 125 used to insert objects into the vagina do not create the air pocket or the suction problems described above.

However, when vaginal-type applicators 125 are used to insert suppositories 130 into the rectum or anal canal 135, many of the same disadvantages associated with finger insertion are exhibited. For example, as the applicator 125 is inserted and then withdrawn from the rectum or anal canal 135, a pocket of air is created and remains in the body as trapped gas where it will eventually be released as flatulence. The passage of gas causes medication not yet absorbed in the rectum to be expelled along with the gas. In addition, withdrawal of the applicator 125 also creates a suction effect that draws the suppository 130 out of an optimal placement position, moving the suppository 130 out toward the anus 140, increasing the likelihood of drug leakage and/or suppository expulsion. Furthermore, vaginal-type applicators are designed for shallow placement of objects (e.g., approximately 4 to 6 centimeters (cm)) and, as a result, cannot optimally position suppositories 130 in which deeper placement is desired.

To mitigate some of the disadvantages associated with inserting a rectal suppository using a finger or known applicators, patients are often instructed to empty their bowel before inserting a suppository. The suppository is then inserted into the patient using the finger insertion technique or known applicators. After the suppository has been inserted, patients are instructed to remain on their left side in the fetal position for at least 30 minutes. In doing so, as a suppository melts and the drug is released, the horizontal position reduces potential leakage as a result of the aforementioned disadvantages. In addition, the user may also be instructed to wear protective hygiene products to protect garments from any medication that is expelled.

Figure 2:
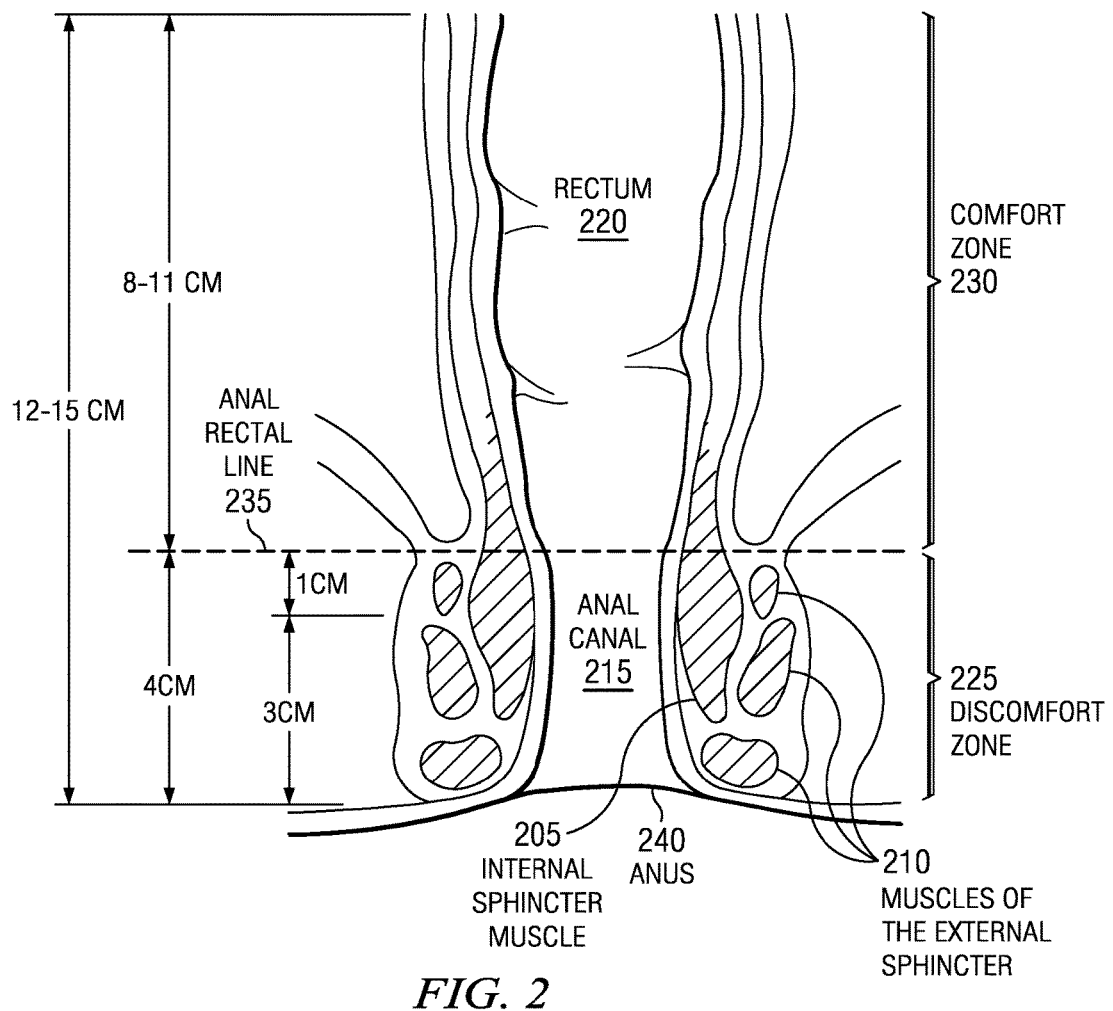
FIG. 2 is an anatomical diagram of a human rectum and anus.

The contrasting effects that occur when vaginal-type applicators are used to insert rectal suppositories in the rectum are due to anatomical differences between the vagina and anal canal. Referring to FIG. 2, the sphincter muscles 205, 210 are circular bands of muscles surrounding the anal canal 215 that consciously and subconsciously contract and relax to control the movement and passage of material through and out of the gastrointestinal tract. Upon reaching the rectum 220, fecal matter is held inside the body by the sphincter muscles 205, 210 until it is convenient to expel the contents of the rectum and anal canal. In contrast, the muscles of the vagina are smooth and flat, and because they do not need to move bulk material through the vagina, they do not subconsciously and spontaneously contract and relax. The vagina lacks the ability to control and prevent the movement and expulsion of material, such as, for example, menstrual flow. Because of this, the formation of air pockets and suction effects described above do not occur in the vagina.

Because the anal canal 215 and the rectum 220 are relatively long (e.g., 10 to 15 cm) as compared with the vaginal canal (e.g., 4 to 6 cm), vaginal-type applicators are not capable of inserting suppositories in the rectum 220 at optimal depths. Certain types of rectal suppositories are more effective, convenient, and comfortable when placed further up the rectum, for example, above the "discomfort zone" 225. As used herein, the discomfort zone 225 refers to an approximately 4 cm section of the anatomy closest to the anus 240, known as the anal canal. This is the section below the anal-rectal demarcation line 235 where a patient's sphincter muscles reside. It is here that fecal matter or other material (e.g., suppository) stimulates the internal sphincter muscles 205 creating a sensation indicating that the bowels need to be emptied. The discomfort zone 225 is also referred to as an "anal trigger zone" and may be used interchangeably herein. The "comfort zone" 230 as used herein refers to a section of the rectum 220 above the discomfort zone 225, that is, a section of the rectum located between approximately 4 cm and 15 cm from the anus 240.

Suppositories positioned within the discomfort zone may stimulate the sphincter muscles 205, 210 causing the urge to defecate, and should a patient do so, all or part of the medication may be expelled along with any fecal matter, reducing the amount of medication available for absorption by the body. Suppositories positioned above the discomfort zone 225, that is, within or above the comfort zone 230, reduce or eliminate the urge to defecate due to stimulation of the sphincter muscles. Additional benefits include less leakage, less likelihood of expulsion, and increased absorption. Increased insertion depth also significantly improves patient convenience by eliminating the 30 minutes patients must currently remain on their side (i.e. horizontal) to ensure adequate absorption. This allows the patient to immediately resume normal day-to-day activities.

It should be noted that although the above anatomical discussions refer to female anatomy, the present invention is by no means limited to females only and example embodiments of the present invention are equally suitable for use with males and females.

FIG. 3A illustrates an example embodiment of an applicator configured to insert a rectal suppository 305 into a human or animal according to the present invention. The applicator may include a barrel 310 and a plunger 315. The barrel 310 has a gripping end 312 and an insertion end 307 and is appropriately sized and shaped to fit within a patient's anal canal. The barrel 310 is further configured to define a gas flow path 320 allowing gas to freely flow through the barrel 310 when positioned within the anal canal. The plunger 315 is configured to be substantially longer than the barrel, thereby allowing the plunger 315 to extend beyond the end of the barrel 310. For example, the barrel 310 may be approximately 4 cm whereas the plunger may be approximately 8 cm.

Thus, the applicator can be configured to insert a suppository 305 above a patient's anal trigger zone. In doing so, the suppository 305 minimizes contact with nerves that trigger the anal muscles that may effect (i.e., reduce) the body's ability to retain and absorb medication provided by the suppository. For example, when a suppository is positioned within the anal trigger zone excessive contact with these nerves may create the urge to release contents within the bowel and, along with these contents, a portion of medication that has been released from the suppository but not yet absorbed by the body. It should be noted that the aforementioned dimensions are merely examples and are not meant to be limiting and alternative dimensions may be similarly used such that the plunger 315 extends beyond the barrel 310.

The plunger 315 may be configured to be movably or slidably coupled to the barrel 310 and is further configured to maintain a second gas flow path 325 that allows gas to freely flow through the plunger 315 as the plunger is withdrawn from the rectum and anal canal after the suppository 305 has been inserted to a desired position. Thus, as the suppository 305 is being inserted, the barrel 310 maintains a gas flow path 320 allowing gas to escape. As the plunger 315 is being withdrawn, the plunger's gas flow path 325 and the barrel's gas flow path 320 are maintained as the plunger is withdrawn from the suppository 305 and the barrel 310 and plunger 315 are removed from the patient's anal canal. The gas flow paths, 325 and 320 allow gas to escape as the barrel 310 and the plunger 315 are removed from the body preventing or reducing the need to release the gas in the form of flatulence.

FIGS. 3B and 3C illustrate end views of an applicator that further includes at least one gas flow path spacing element 330, 335 configured to maintain the barrel's 310 gas flow path 320. Referring to FIG. 3B, the barrel 310 includes the at least one gas flow path spacing element 330 where the spacing element extends inward from an inner wall of the barrel 310 to contact the outer wall of the plunger 315, thereby maintaining barrel's gas flow path 320. Since the plunger 315 is hollow, a second gas flow path 325 is maintained within the plunger 315 as well. FIG. 3C illustrates an alternative example embodiment where the at least one gas flow path spacing element 335 extends outward from an outer wall of the plunger 315 to contact an inner wall of the barrel 310 to maintain the barrel's gas flow path 320. Also shown is the at least one second gas flow path 325 maintained by a similarly hollow plunger 315. Alternatively, at least two gas flow path spacing elements may simultaneously extend inward from the inner surface of the barrel 310 and outward from the outer surface of the plunger 315 to maintain the first gas flow path 320.

Figure 4A:
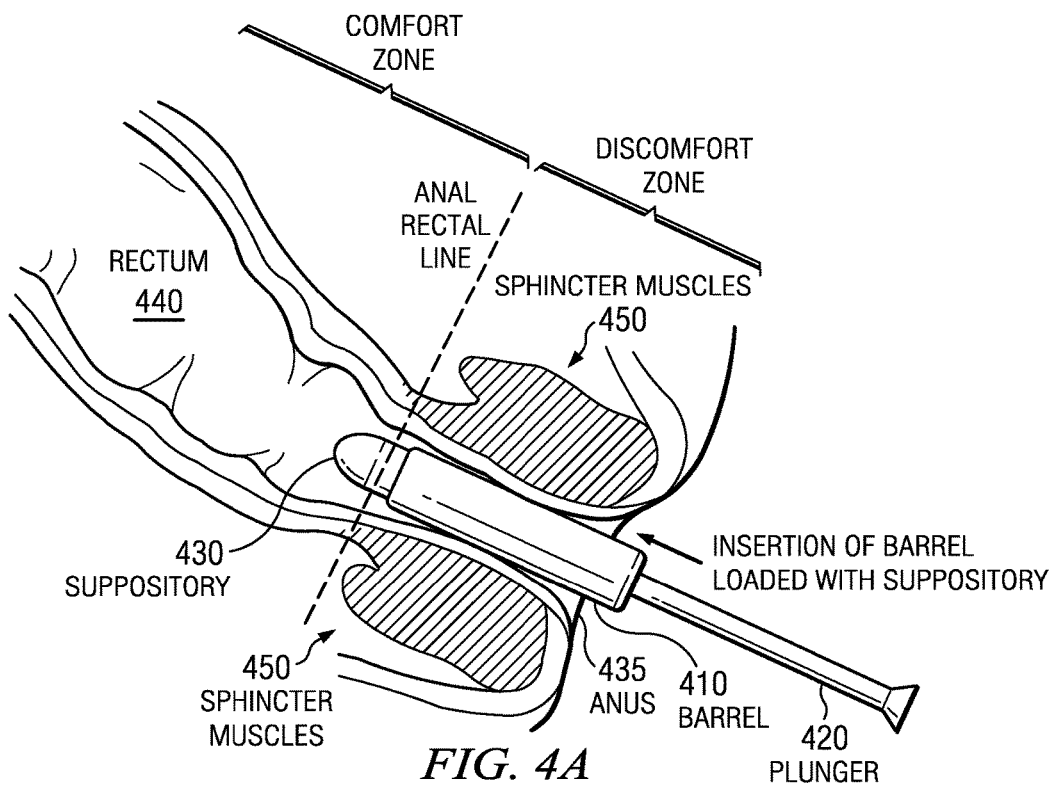
FIGS. 4A-C are anatomical diagrams illustrating an example embodiment of the invention in various states of use.
Figure 4B:
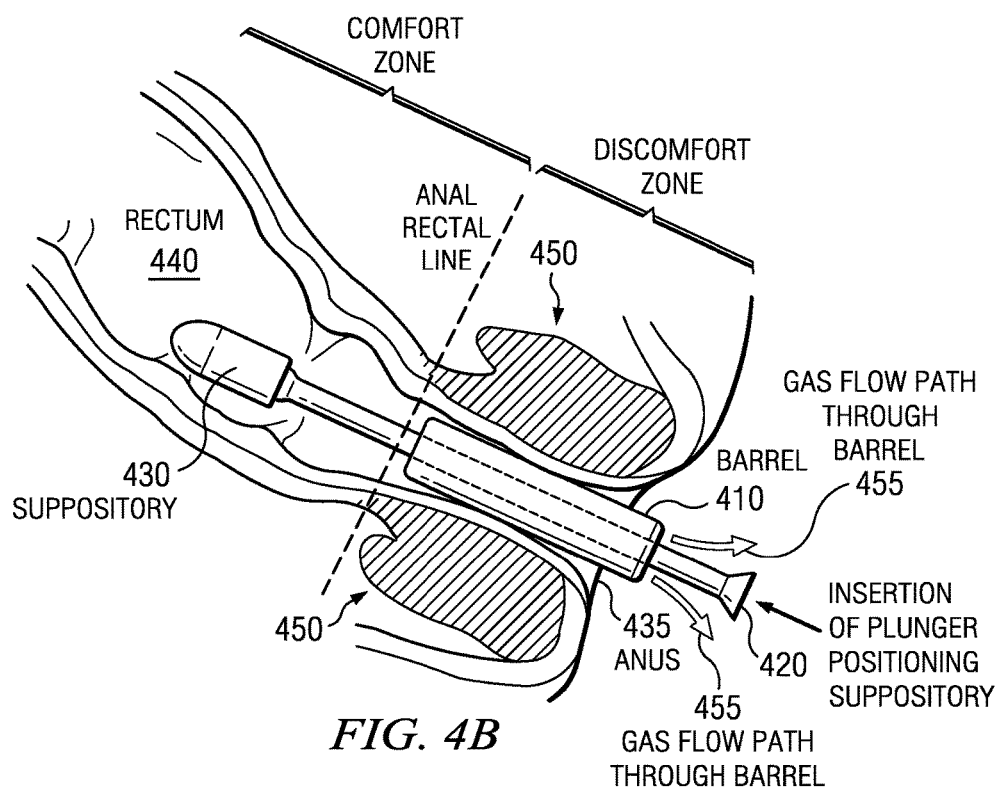
Figure 4C:
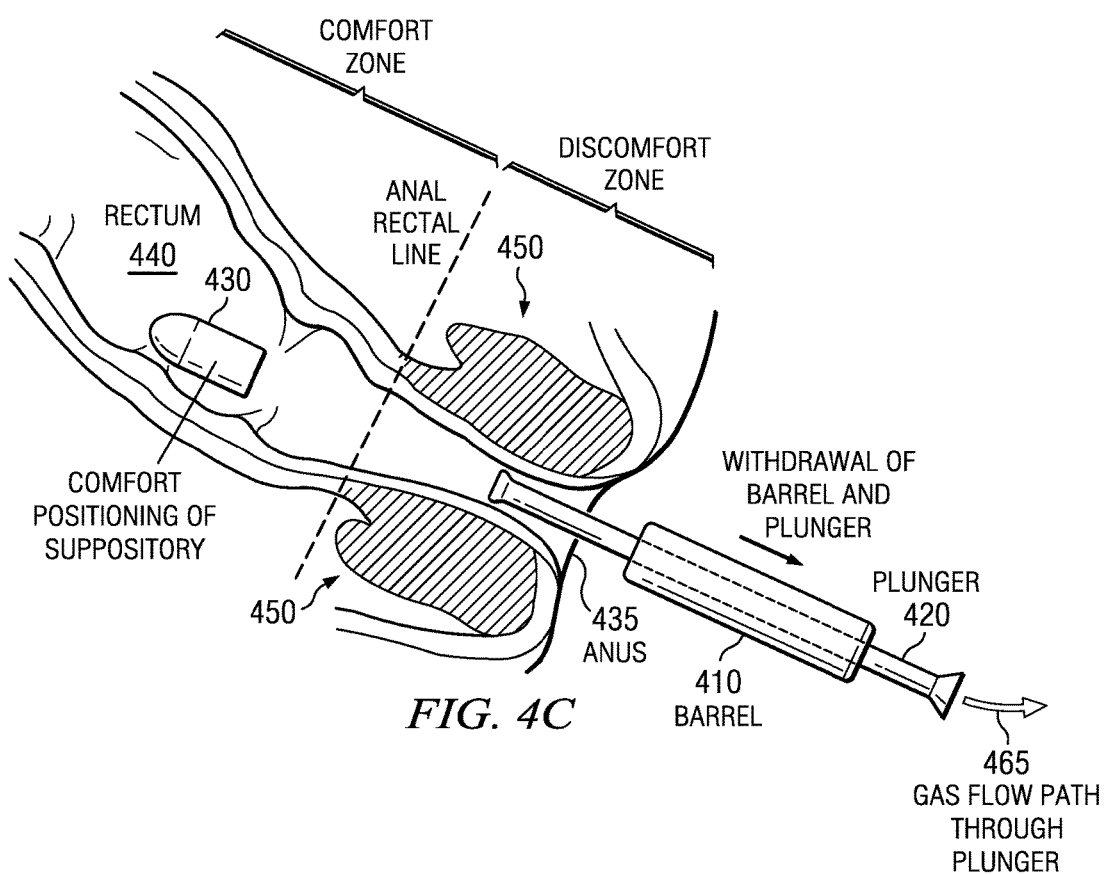

FIGS. 4A-C illustrate an example embodiment employing an applicator to insert a suppository 430 into a patient's rectum 440 in varying states of use. The applicator may include a barrel 410 and a plunger 420. Referring to FIG. 4A, the plunger 420 is positioned within the barrel and the suppository 430 is loaded into the barrel 410. The applicator is then inserted into the patient's anus 435. Referring to FIG. 4B, the plunger is depressed such that the suppository 430 is inserted within the rectum 440 to a desired position, such as a location within a comfort zone above the patient's sphincter muscles 450 (i.e., above an anal trigger zone). As the plunger 420 is inserted or pushed into the barrel, the barrel 410 maintains a first gas flow 455 such that any trapped air may escape through the barrel 410 to outside the patient's anus 435. Referring now to FIG. 4C, once the suppository has been positioned in the desired location, the applicator may be removed from the patient's rectum 440. As the plunger 420 is removed, suction effects due to withdrawal of the plunger 420 are prevented by venting any pressure or vacuum buildup through the second gas flow path 465 maintained by the plunger 420.

Figure 4E:
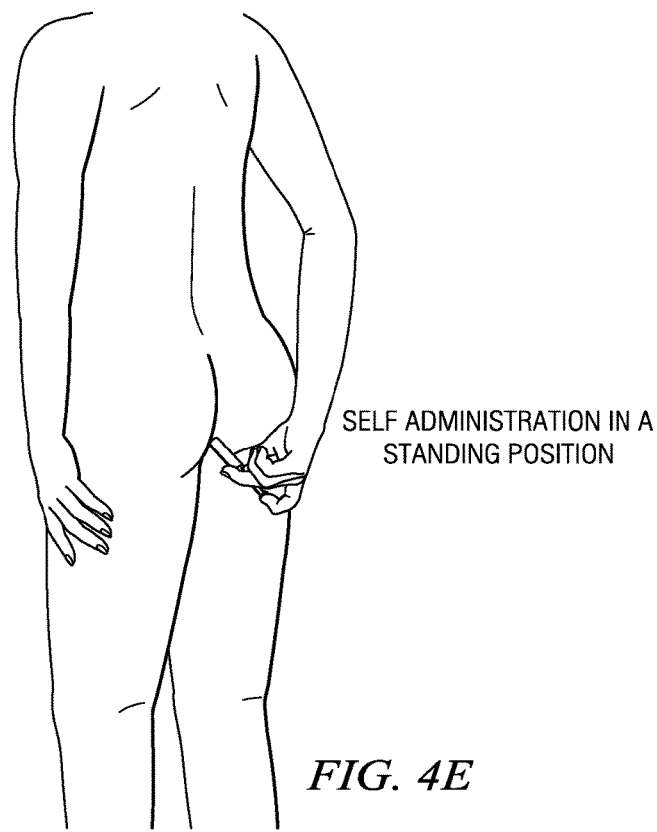
FIG. 4E illustrates inserting a rectal suppository in a standing position according to an example embodiment.
Figure 4D:
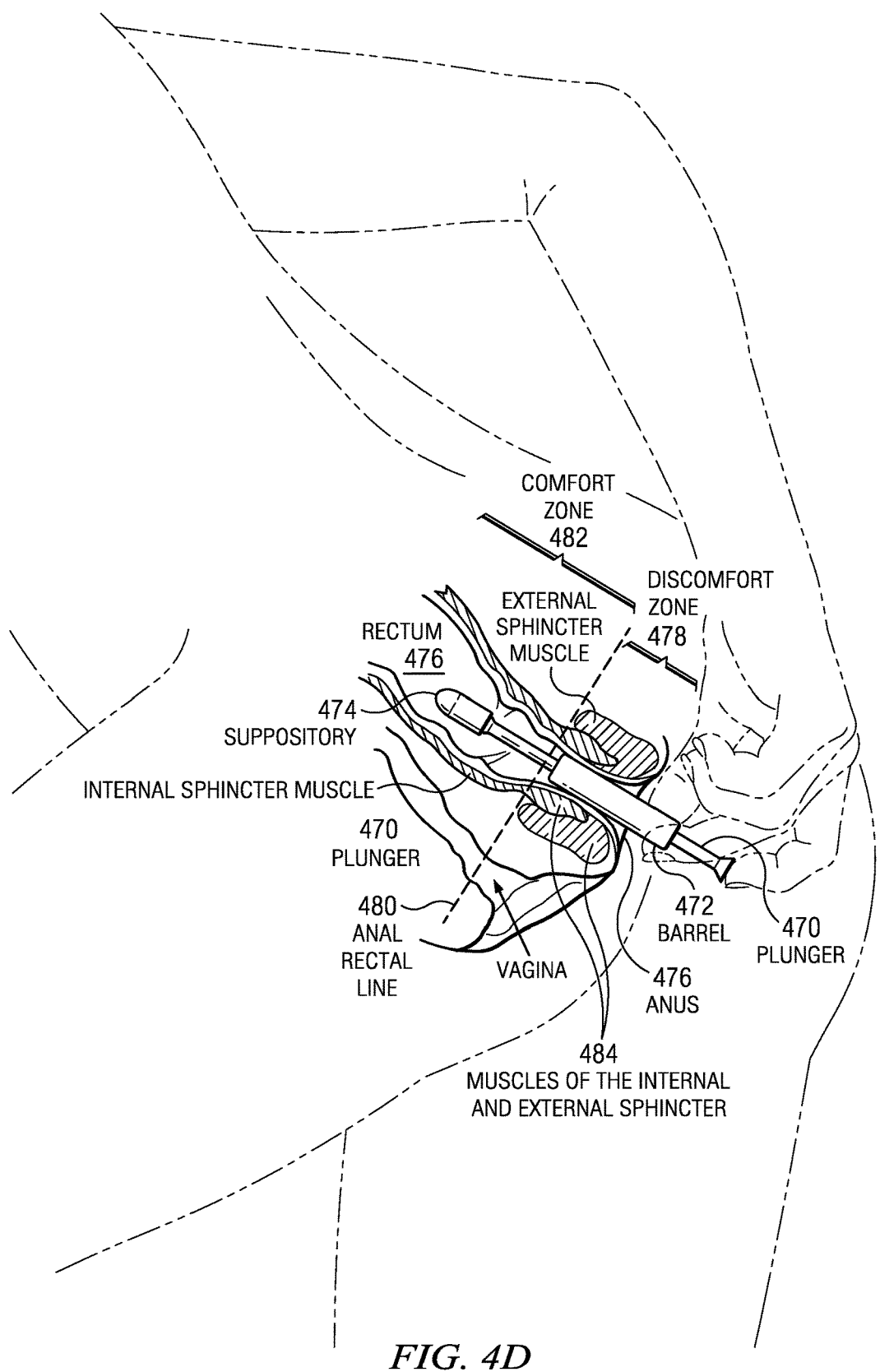
FIG. 4D is a larger perspective anatomical diagram illustrating an example embodiment of the invention.

FIG. 4D is a larger perspective anatomical diagram illustrating a patient employing an applicator to self-administer a rectal suppository according to an example embodiment of the invention. The applicator may include a plunger 470 and barrel 472 configured to insert a suppository 474 into a patient's rectum 476. The barrel 472, plunger 470, and suppository 474, are positioned at the patient's anus 476 and then inserted into the patient. The barrel 472 typically does not extend beyond the anal-rectal line 480, that is, remains within the discomfort zone 478, although the example embodiment is not limited as such and the barrel 472 may extend into the patient's comfort zone 482. Once the applicator has been positioned properly, the patient may depress the plunger 470 to cause the suppository 474 to be placed in a desired position, such as an area within the comfort zone 482 of the rectum 476. As the user withdraws the applicator, trapped air or suction effects may be vented via a first or second gas flow path maintained by the barrel 472 or plunger 470, respectively.

As a result, the applicator may be used to mitigate the ergonomic difficulties presented when self-administering rectal suppositories. The applicator also reduces trapped gas and suppository 474 movement upon insertion and withdrawal, and reduces leakage or expulsion due to stimulation of the sphincter muscles 484. In addition, placement within the patient's comfort zone 482 may also allow the patient to resume their day-to-day activities almost immediately (rather than remaining in a horizontal position until the suppository has dissolved and medication has been absorbed). Consequently, patients may be more likely to continue their prescribed treatment course allowing the patient to obtain full benefit of the suppository's medication. This may result in reduced complications, hospitalization, and/or placing a patient on a stronger drug regime due to noncompliance. Thus, effective delivery of rectal suppositories provided by example embodiment of the present invention may improve patient health and well-being. It should be noted that the above description equally applies when, for example, another person, such as healthcare personnel employs the applicator to insert a suppository into a patient or animal.

FIG. 4E illustrates a method for inserting a rectal suppository in a standing position according to an example embodiment of the present invention. Self-administration of rectal suppositories can be especially challenging due to the body mechanics required to adequately align, position, and insert the suppository as well as a reduced line of sight toward an insertion point. Body mechanics and line of sight issues make self-administration even more difficult when the patient is in a standing position. Consequently, self-administration while in a standing position is often not a viable option for many patients. However, employing an applicator according to the present invention enables a patient to overcome these issues by providing increased depth positioning ability and control. Thus, a patient can use the applicator of the present invention to self-administer a rectal suppository while in a number of different positions including standing, squatting, sitting, prone, fetal, or other positions.

The example embodiments illustrated in FIGS. 3A-C and 4A-C are examples of a plunger and barrel configured to maintain a first and second gas flow path. However, numerous other barrel and plunger configurations are envisioned where a first and second gas flow path are maintained within the barrel and plunger, respectively.

Figure 5A:
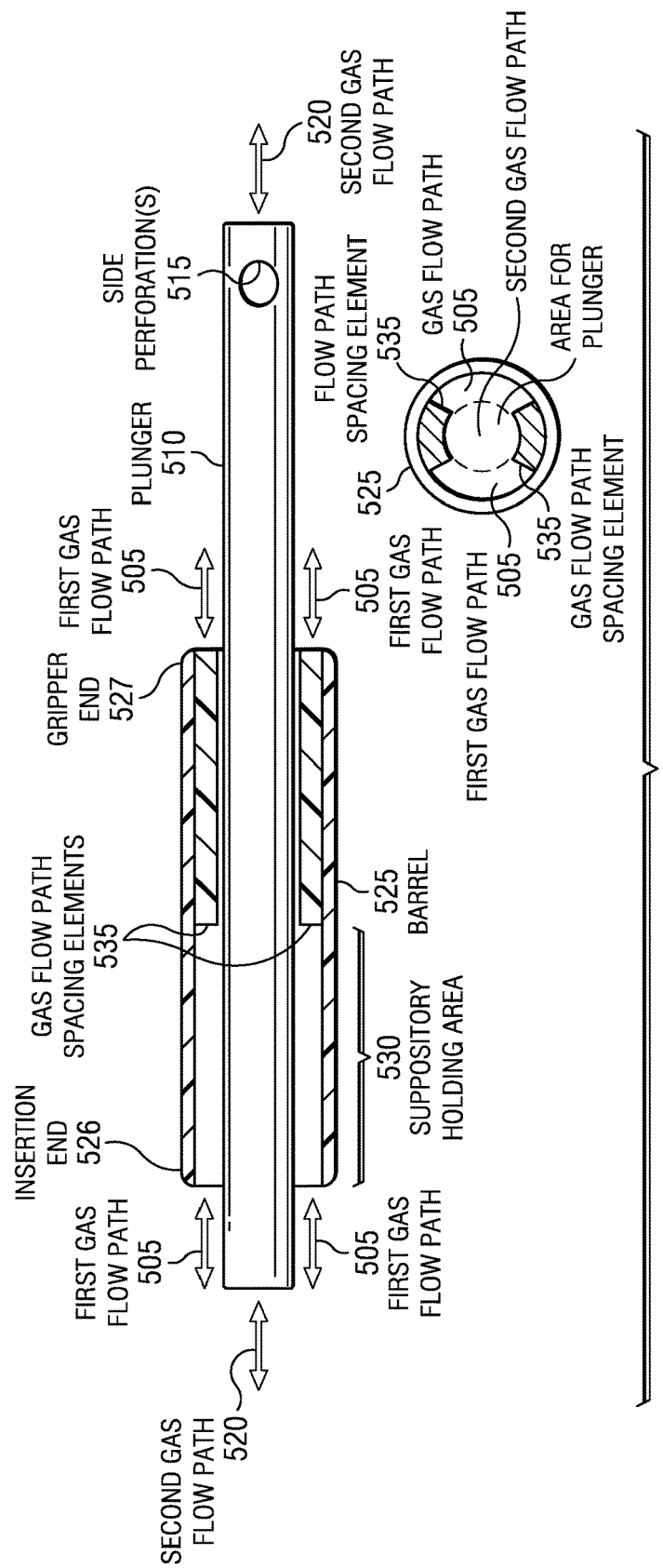
FIGS. 5A-B illustrate alternative example embodiments of the invention.

For example, FIG. 5A illustrates an example embodiment where a barrel maintains a first gas flow path 505 and a plunger 510 having side perforations 515 configured to maintain or augment at least one second gas flow 520. Gas flow path spacing elements 535 may extend inward from the barrel 525 to contact the plunger 510. Gas flow path spacing elements 535 may be configured to provide a suppository holding area 530 during insertion of the apparatus into the anal canal. Alternatively, or in addition, the gas flow path spacing elements 535 may extend from the outer surface of the plunger 510 to contact the inner surface of the barrel 525.

Figure 5B:
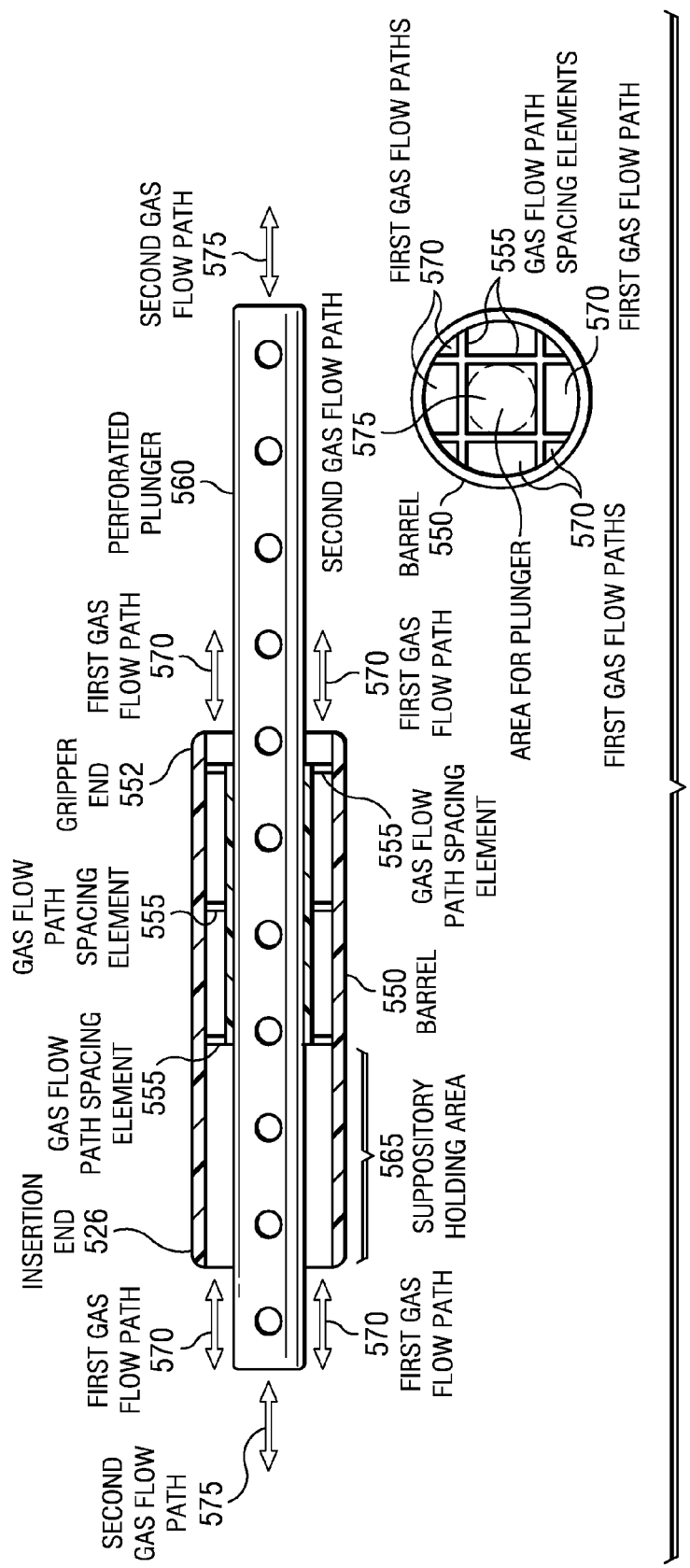

FIG. 5B illustrates another example embodiment depicting a barrel 550 that includes gas flow path spacing elements 555 configured in a horizontal and vertical arrangement to maintain the first gas flow path 570. In addition, the plunger 560 includes multiple perforations in order to maintain or augment the second gas flow path 575 maintained by the plunger 560. Alternatively, the plunger 560 may be replaced with a solid (i.e., non-hollow) plunger where the gas flow path spacing elements extend outward from the plunger to press on tissue between the anal canal or rectum and the plunger. In this manner, the second gas flow path is maintained in the space created between the solid plunger and the anal canal or rectum.

Note that the gas flow path spacing elements 535, 555 in FIGS. 5A and 5B may extend from a gripper end 527, 552 of the barrel 525, 550 to a point before the insertion end 526, 551 such that the absence of the gas flow path spacing elements 535, 555 can support a suppository partially or completely below an open end of the barrel's insertion end. This feature allows the user to place the suppository into a holding area 530, 565 at the insertion end of the barrel 525, 550 to support the suppository prior to and during insertion of the applicator.

Figure 6A:
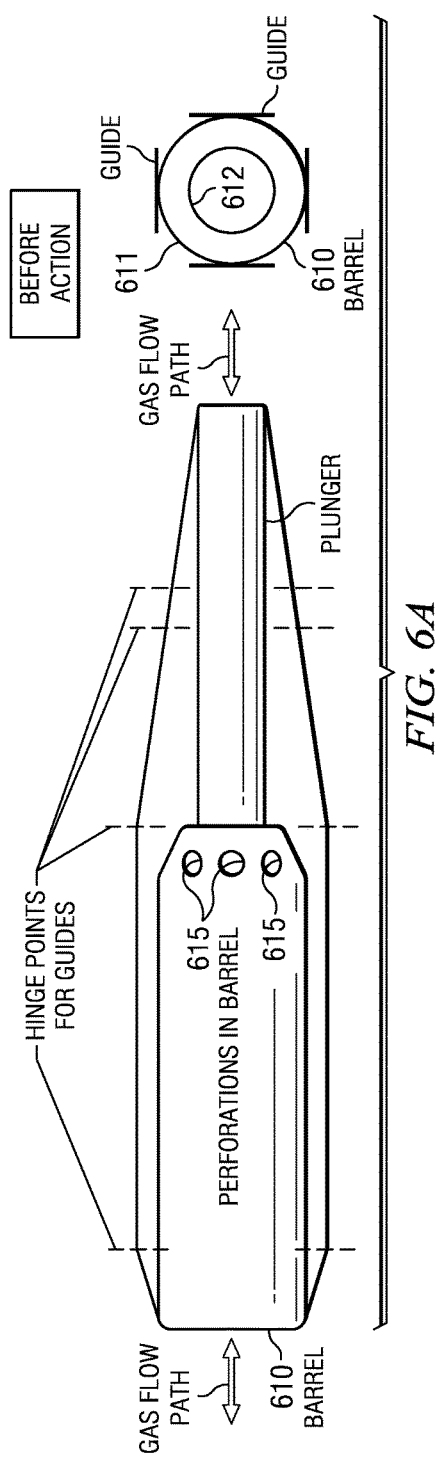
FIGS. 6A-C illustrate additional alternative example embodiments of the invention.
Figure 6B:
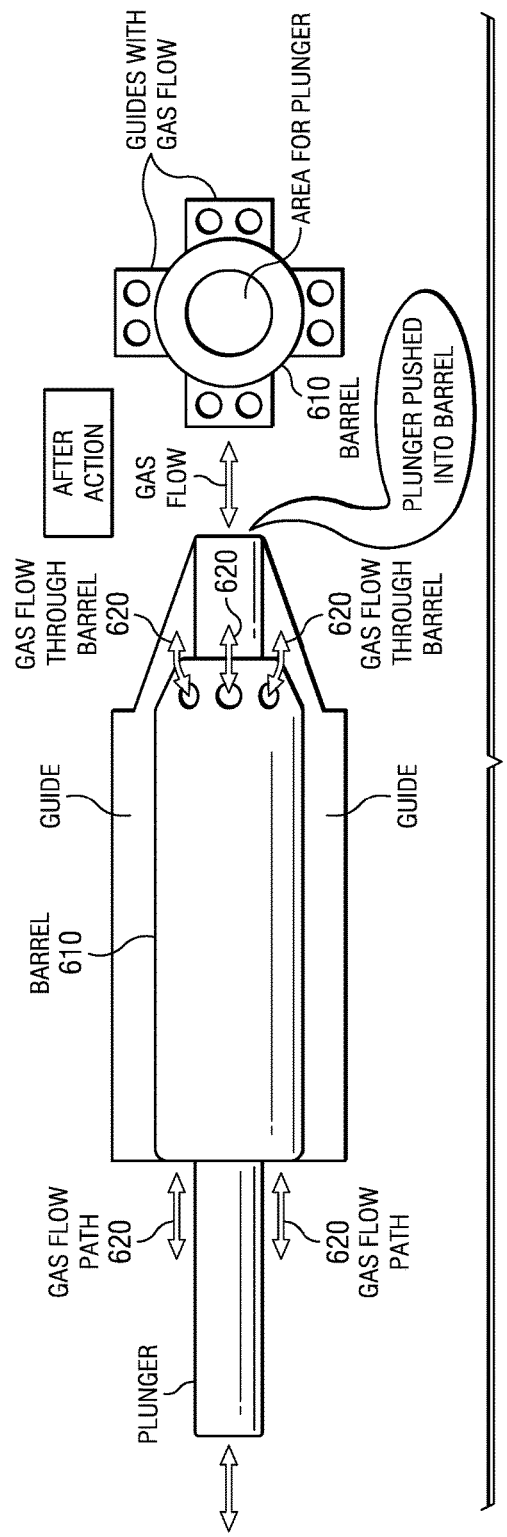

FIGS. 6A and 6B illustrate an example embodiment including a double walled barrel 610 with perforations 615 configured to maintain or augment a first gas flow path 620. The barrel 610 has an inner wall 612 coupled to an outer wall 611 that defines a hollow tube to allow gas to flow through the inner 612 and outer 611 walls of the barrel 610. Thus, in this embodiment, the area between the barrel's inner 612 and outer 611 walls maintain the first gas flow path 620. FIG. 6A illustrates the applicator before a suppository is positioned and FIG. 6B illustrates the applicator after the suppository has been placed in the desired position.

Figure 6C:
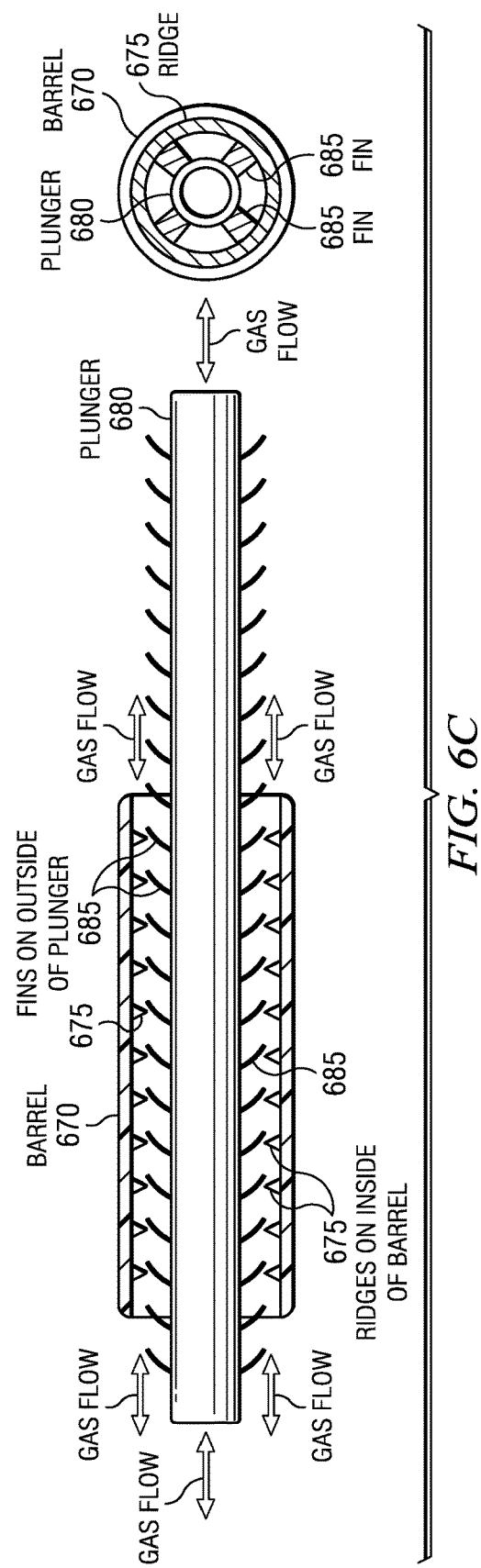

FIG. 6C illustrates yet another alternative example embodiment where the barrel 670 includes ridges 675 along the inner surface of the barrel 670 and the plunger 680 includes fins 685 extending outward from the outer surface of the plunger 680 to the inner surface of the barrel 670. The fins 685 may be configured in a horizontal and/or vertical configuration such that the barrel maintains the first gas flow path. The fins 685 in conjunction with the ridges 675 may increase depth control and placement accuracy.

Figure 7A:
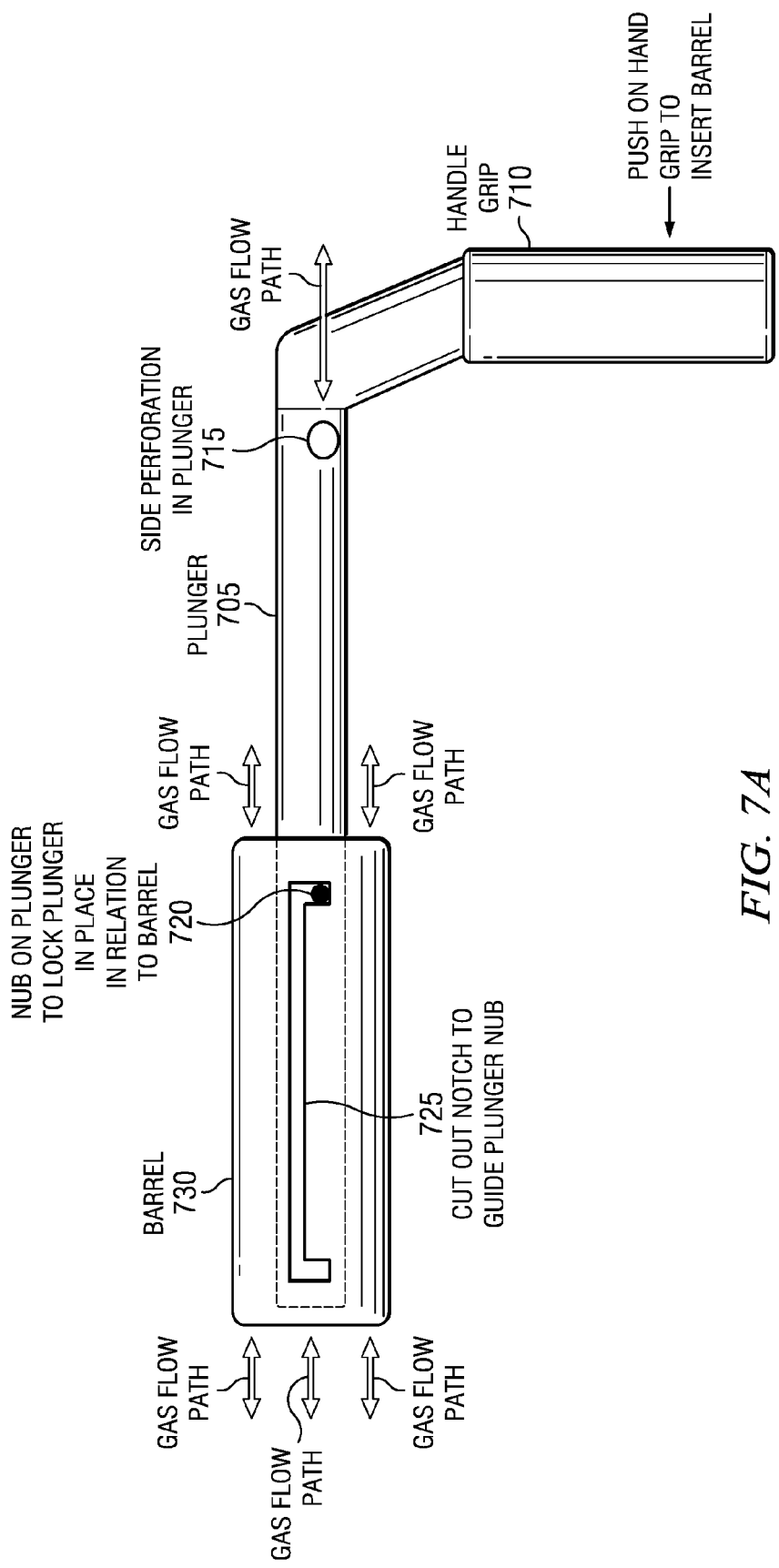
FIGS. 7A-C illustrate alternative example embodiments of the invention configured for use by patients or medical personnel with limited dexterity.
Figure 7B:
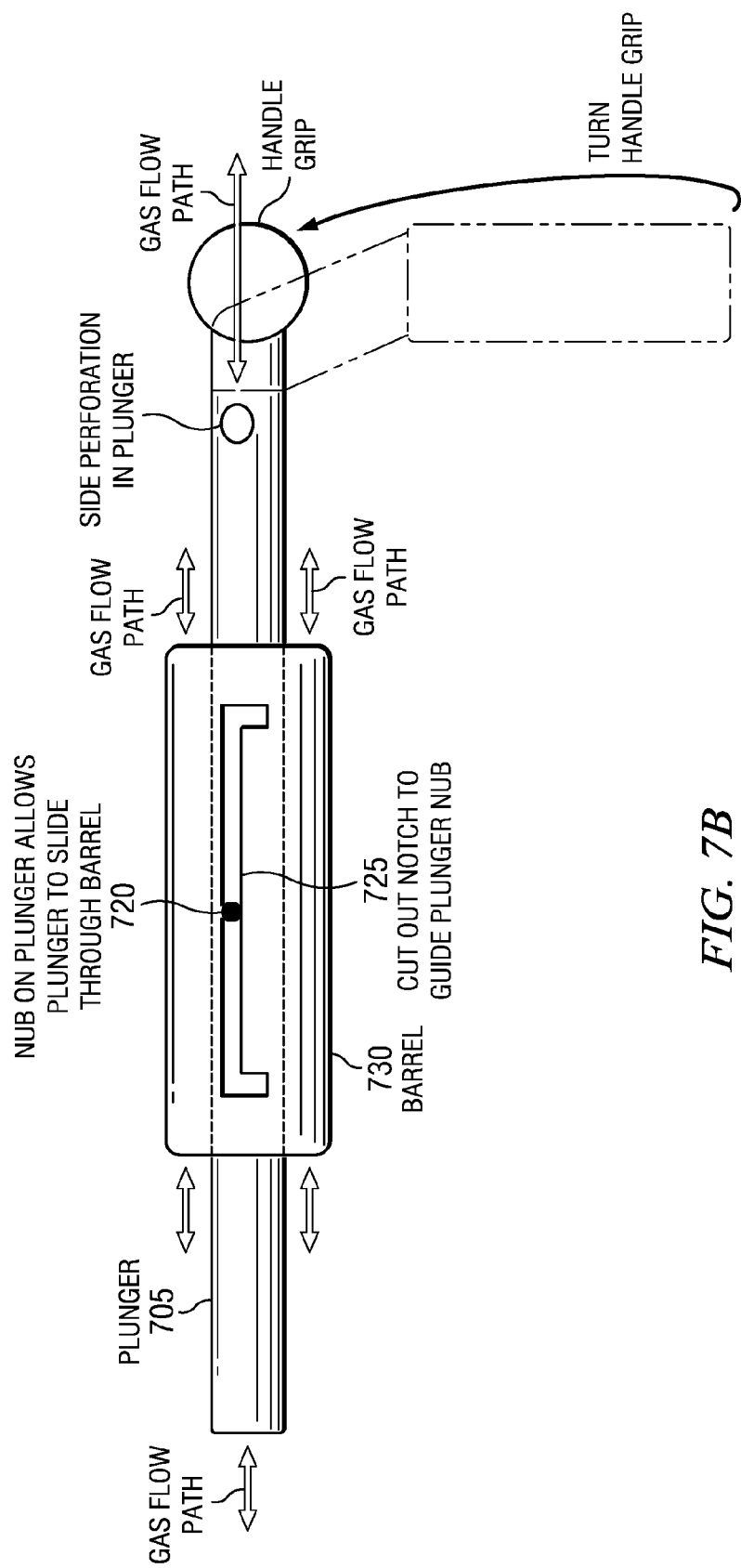
Figure 7C:
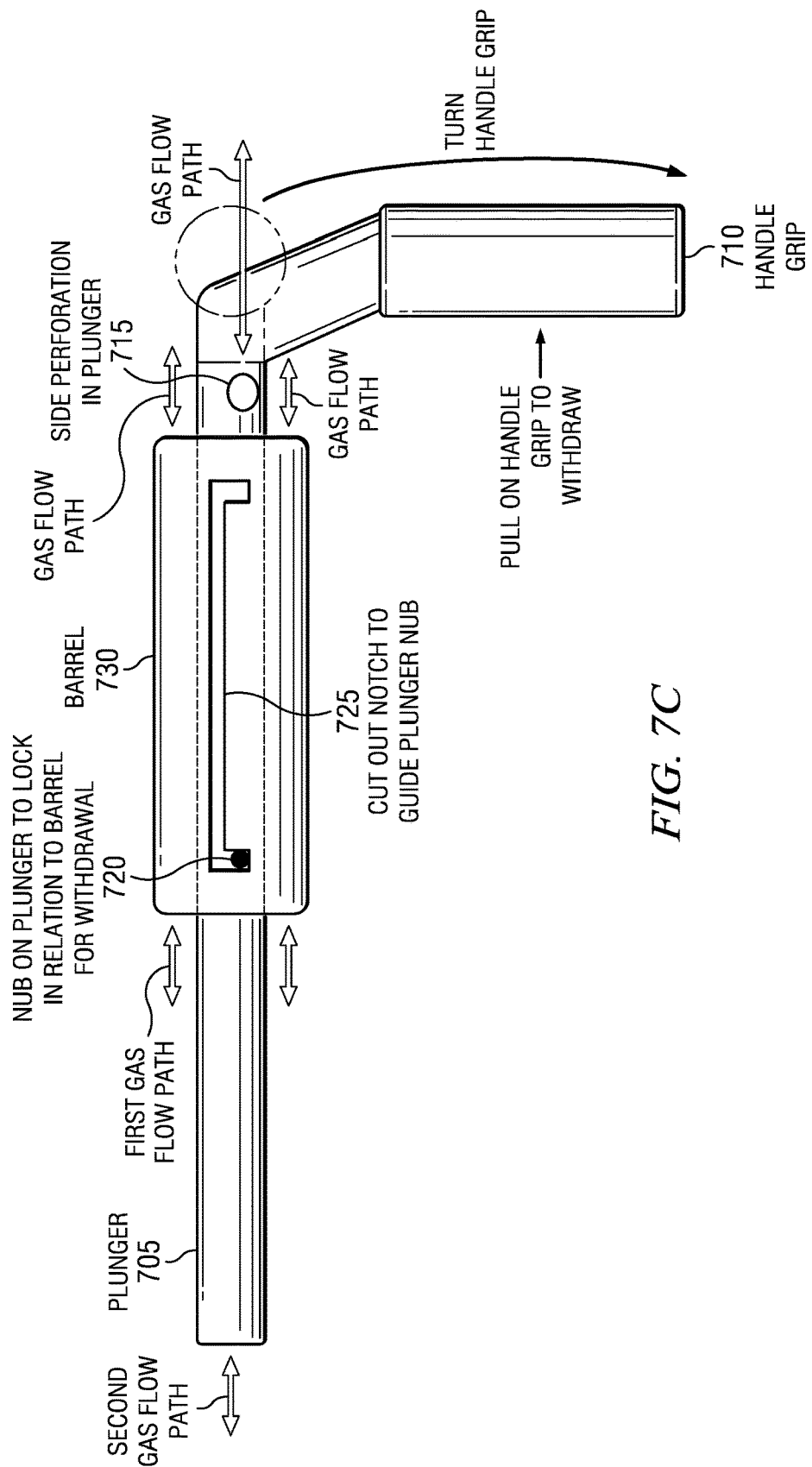

FIG. 7A-C illustrates still another example embodiment of an applicator that provides additional features for use by patients with limited dexterity. In this embodiment, a plunger 705 is movably coupled to a barrel 730 where the plunger 705 includes a handgrip 710 at a hand interface end configured to facilitate manipulation of the plunger 705. The plunger 705 may also include one or more side perforations 715 to maintain or augment a second gas flow path. The plunger 705 may also include a nub 720 that may be configured to slide within a notch 725 formed in the barrel 730. In FIG. 7A, the nub 720 is in a starting position.

FIG. 7B illustrates the nub 720 and notch 725 engagement as the plunger 705 extends through the barrel 730 during insertion of a suppository. To initiate a slidable movement of the plunger 705, the handgrip 710 is rotated to align the nub 720 with the longitudinal section of the notch 725 to release the nub 720 from a starting fixed position to allow the plunger 705 to slide within the barrel 730. The handgrip 710 is depressed until the plunger 705 is fully extended within the barrel 730.

FIG. 7C illustrates the nub 720 locked in a fully extended position after the suppository has been placed into a desired location prior to removal of the applicator. After the hand grip 710 has been fully depressed, it can be locked in a fixed position by rotating the handgrip 710 so that the nub 720 is positioned in the lock position. The applicator may be removed by reversing the procedure.

Figure 8A:
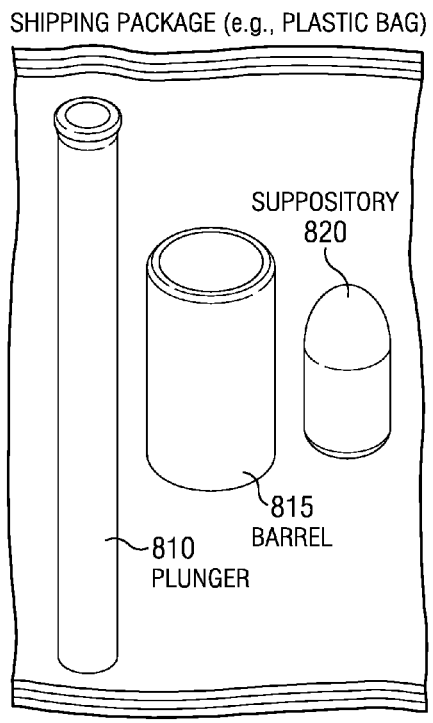
FIGS. 8 A-C are perspective views of an apparatus packaged for sanitary use according to example embodiments of the invention.

FIG. 8A illustrates a kit in a packaging container for use in shipping, storing, transporting, and maintaining an applicator configured to insert a rectal suppository in a hygienic and protected state prior to use. The kit may include a plunger 810, barrel 815, and suppository 820. The packaging container may be formed using various materials, such as plastic or foil. For example, the package may include a top and bottom layer of 3-mil plastic sheets heat-sealed at the edges to provide hygienic, airtight package. A notch (not shown) may also be included to allow ease of opening and removal of the applicator. The kit provides a mechanism to conveniently co-locate the items necessary to administer the suppository 820 for home and/or travel use.

Figure 8B:
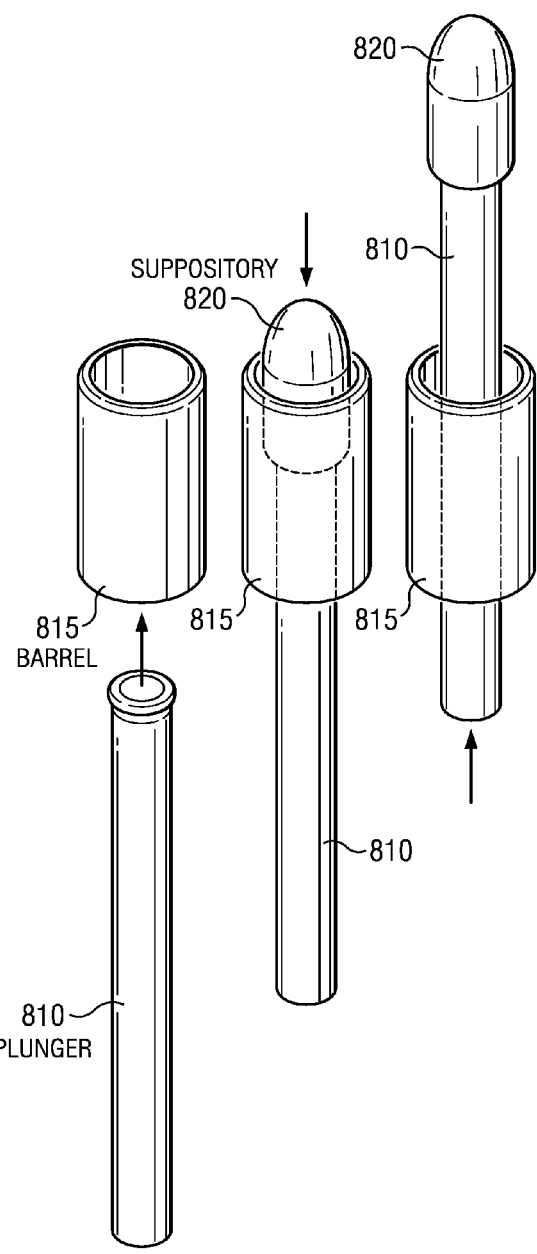

FIG. 8B depicts the applicator in various stages of use. First, the plunger 810 is inserted into the barrel 815. Next, the suppository 820 may be inserted into the barrel 815 in, for example, a suppository holding area (not shown). The barrel 815 is then inserted into the anal canal. The plunger 810 is depressed to position the suppository 820 to the desired location within the anal canal or rectum, for example, above a user's anal trigger zone. Note that during insertion, the barrel 815 maintains a first gas flow path. During withdrawal, the barrel 815 continues to maintain the first gas flow path and the plunger 810 maintains a second gas flow path. Thus, any gas that may have created an air pocket during insertion is allowed to escape and, in addition, any potential suction is similarly alleviated.

It should be noted that although the above sequence describes the plunger 810 being inserted into the barrel 815 as the first step, it may also be possible for the suppository 820 to be inserted into the barrel 810 as a first step. The order in which the components are configured together may be interchangeable and the present invention is not limited by the order thereof.

Figure 8C:
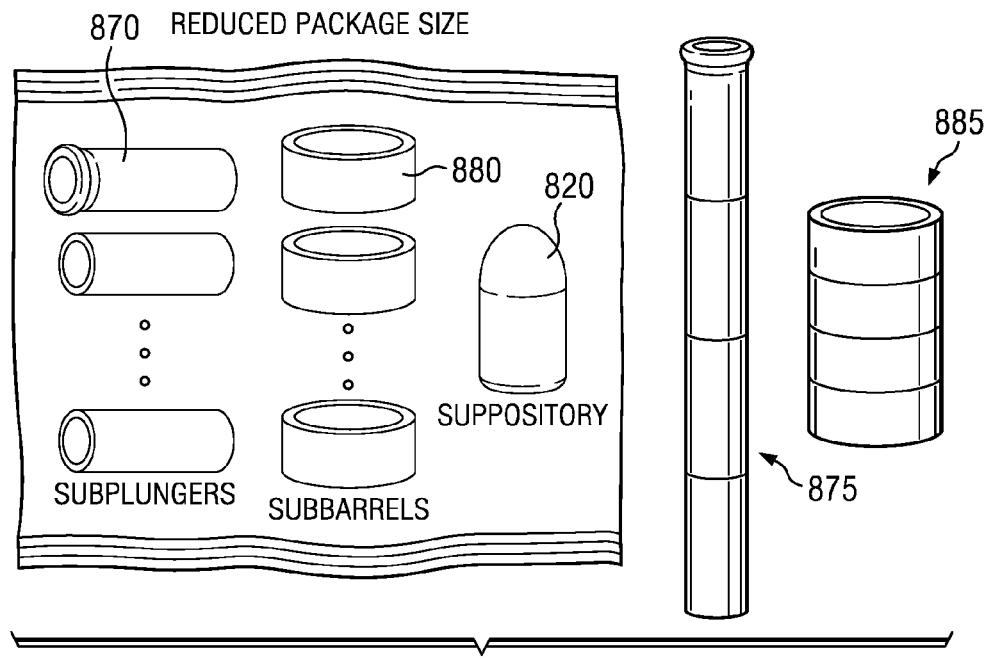

FIG. 8C illustrates an alternative example embodiment of an applicator configured to be packaged in a reduced sized container. Here, the two or more sub-plungers 870 may be assembled to create a single plunger of sufficient length 875. Similarly, two or more sub-barrels 880 may be assembled to create a single barrel 885 of appropriate size where the barrel 885 has a gripper end and an insertion end. Once assembled, the plunger 875 and barrel 885 operate in a similar manner as that described above in various example embodiments. The reduced package size embodiment may be particularly well suited for carrying in, for example, a pocketbook, pocket, or other location on or near a person.

Figure 9:
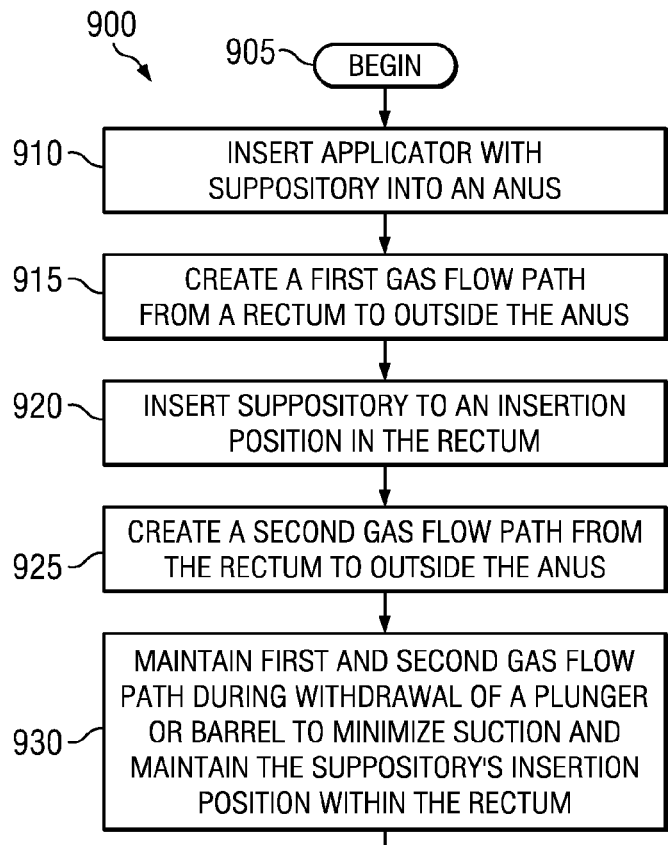
FIG. 9 is a flow diagram illustrating a procedure performed in accordance with an example embodiment of the invention.

FIG. 9 is a flow diagram 900 illustrating an example procedure for inserting a rectal suppository performed in accordance with example embodiments of the present invention. The procedure 900 begins at block 905 and proceeds to block 910 where an application with a suppository are inserted into the anus. At block 915, a first gas flow path extending from a patient's rectum and/or anal canal to outside the patient's anus is created and maintained. At block 920, a suppository is further inserted to a particular insertion position within the patient's rectum while simultaneously maintaining the first gas flow path. At block 925, a second gas flow path extending from the patient's rectum to outside the patient's anus is also created. At block 930, the first and second gas flow paths are maintained as the plunger and/or barrel are withdrawn from the patient so as to minimize suction on the suppository and vent gas, thereby ensuring the suppository maintains the desired insertion position within the rectum and minimizing the gas trapped in the body. It should be noted that the order in which the barrel and plunger are removed can be varied, i.e., the plunger may be removed before, during, or after the barrel is removed. The procedure 900 then ends at block 935.

It should be readily appreciated by those of ordinary skill in the art that the aforementioned blocks are merely examples and that the present invention is in no way limited to the number of blocks or the ordering of blocks described above. For example, some of the illustrated blocks may be performed in an order other than that which is described or include more or fewer blocks. Moreover, it should be understood that various modifications and changes may be made to one or more blocks without departing from the broader scope of the present invention. It should also be appreciated that not all of the illustrated flow diagram is required to be performed, that additional flow diagram(s) may be added or substituted with other flow diagram(s).

Example embodiments of an apparatus for inserting a suppository, such as a plunger or a barrel of a suppository applicator, may include features for use by patients with limited dexterity, e.g., patients with arthritis. These features can include ridges or raised portions on an outside wall of the apparatus, or grooves or notches at a finger-interface end, to facilitate gripping of the apparatus and provide tactile feedback to the user. Other features can include portions of the apparatus that have a larger diameter to facilitate manipulation of the apparatus, e.g., a gripping end having a larger diameter than the body of the apparatus. For example, a plunger that includes an insertion end having a larger diameter than the body of the plunger can prevent the plunger from separating or falling out of the barrel of the assembled applicator. Other features allow a patient or user to adjust the apparatus, e.g., the barrel, to accommodate suppositories of different sizes.

Figure 10A:
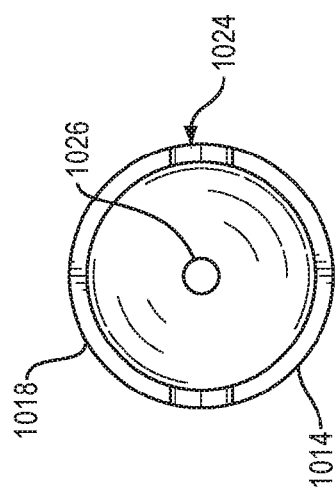
FIGS. 10A-C are respective front, side, and back views of an example embodiment of the invention.
Figure 10C:
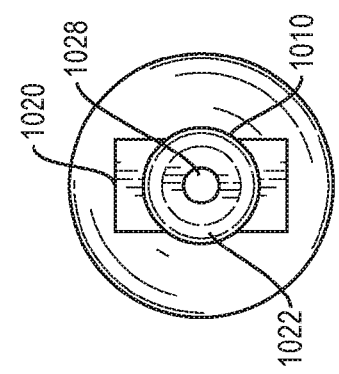
Figure 10B:
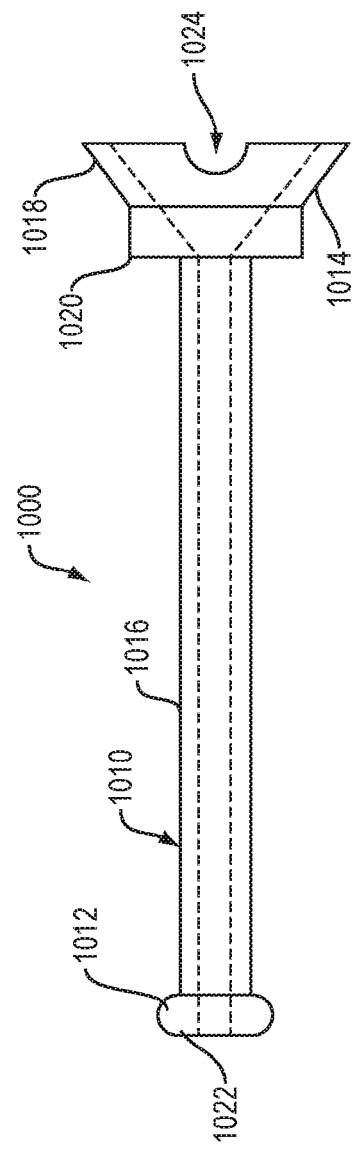

FIGS. 10A-10C are respective front, side, and back views of an example embodiment of an apparatus 1000 for inserting a suppository into an animal or human. Apparatus 1000 includes body 1010 having an insertion end 1012, a hand or finger-interface end 1014, and a central portion 1016 that extends between the insertion end 1012 and the hand or finger-interface end 1014. As shown, the body 1010 can be substantially cylindrical and elongated. The body 1010 can be dimensioned for insertion of a suppository into an anal canal or rectum, similar to the plungers described in reference to FIGS. 3 and 4 or elsewhere herein. The interface end 1014 includes an interface portion 1018 to interface with a hand or finger. The interface end 1014 further includes a stepped portion 1020 that is wider than the central portion 1016 and positioned between the central portion 1016 and the interface portion 1018. In this embodiment, the stepped portion 1020 does not extend around the entire circumference of the body 1010. As illustrated in FIG. 10A, the stepped portion 1020 can be rectangular, although it need not be.

In the embodiment of FIGS. 10A-10C, the body 1010 of the apparatus defines a hollow structure, such as a hollow tube or hollow plunger. The body 1010 includes an opening 1026 at the interface end 1014 that is in fluid communication with an opening 1028 at the insertion end 1012. The hollow structure is configured to maintain a gas flow path, such as the gas flow paths described in reference to the plunger embodiments of FIGS. 3A-3C, 4A-4D, 5A-5B, 6A-6C, 7A-7C, and 8A-8B.

Figure 10D:
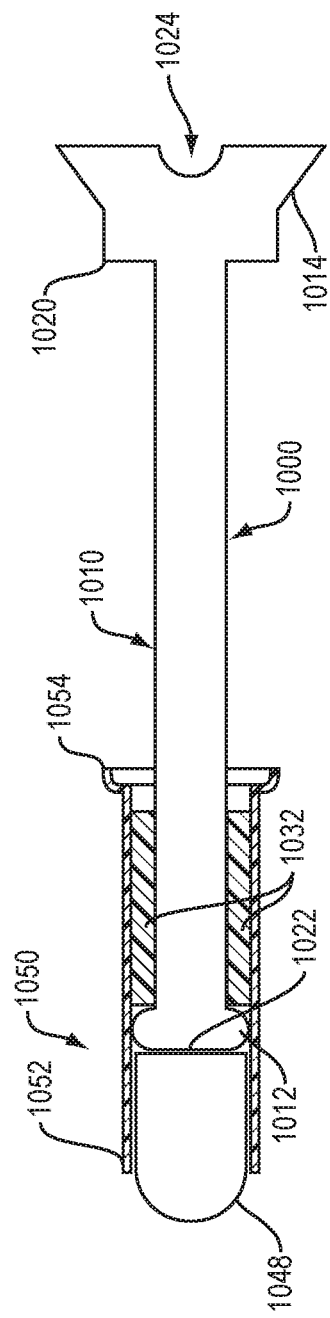
FIG. 10D is an illustrations of an apparatus for inserting a suppository according to an example embodiment of the invention.

As shown in FIGS. 10A and 10B, the insertion end 1012 can include a suppository interface portion 1022 configured to contact with a suppository (see, e.g., FIG. 10D). The suppository interface portion 1012 may be as wide as or wider than a portion of a suppository with which the interface portion 1012 is configured to contact. Alternatively, the suppository interface portion may be narrower than a portion of a suppository with which the interface portion is configured to contact. Furthermore, the insertion end 1012 has a larger diameter than the central portion 1016.

The interface portion 1018 of the hand or finger-interface end 1014 may be cup-shaped, as illustrated in FIGS. 10B-10C, or otherwise configured to accept a tip of a finger. The interface portion 1018 can include at least one opening, groove, or notch 1024 in a sidewall of the interface portion 1018. The opening or notch 1024 allows for gas to flow when a finger is in contact with the interface portion 1018 such that the apparatus can maintain a gas flow path through opening 1026.

FIG. 10D is an illustration of an apparatus for inserting a suppository according to an example embodiment of the invention. The figure illustrates an applicator that includes the apparatus 1000 of FIG. 10A-C as an inner member, e.g., a plunger, which is slidably positioned in an outer hollow member 1050, e.g., a barrel. The outer hollow member 1050 includes a gripping end 1054 and an insertion end 1052. A suppository 1048 is placed inside the outer member 1050 at the insertion end 1052. The suppository interface portion 1022 of the insertion end of the inner member contacts the suppository 1048. Similar to the embodiments described in reference to FIGS. 3 and 4, the assembly shown in FIG. 10D can be used to insert a suppository in an anal canal or rectum. Similar to the applicator described in reference to FIG. 3, the applicator of FIG. 10D includes at least one gas flow path spacing element 1032 configured to maintain a gas flow path of the outer member, e.g., barrel, 1050. As shown, the outer member 1050 includes the at least one gas flow path spacing element 1032. The spacing element extends inward from an inner wall of the outer member 1050 to contact the outer wall of the body 1010 of the inner member, e.g., plunger, 1000, thereby maintaining the outer member's gas flow path. Since the inner member, e.g., plunger, 1000 is hollow, a second gas flow path is maintained within the inner member 1000 as well. One or more notches 1024 at the interface end 1014 ensure that the second gas flow path is not obstructed by a user's finger contacting the interface portion during use. Furthermore, the diameter of the insertion end 1012 is wider than the diameter of the body 1010. The wider diameter of the insertion end 1012 prevents the inner member, e.g., plunger, 1000 from sliding past the spacing element(s) 1032 and away from the suppository 1048. Consequently, the wider diameter of the insertion end 1012 prevents the inner member from accidentally falling out of the gripping end 1054 of the outer member, e.g., barrel, 1050 when a patient, such as a patient with limited dexterity, is handling the applicator.

Figure 10E:
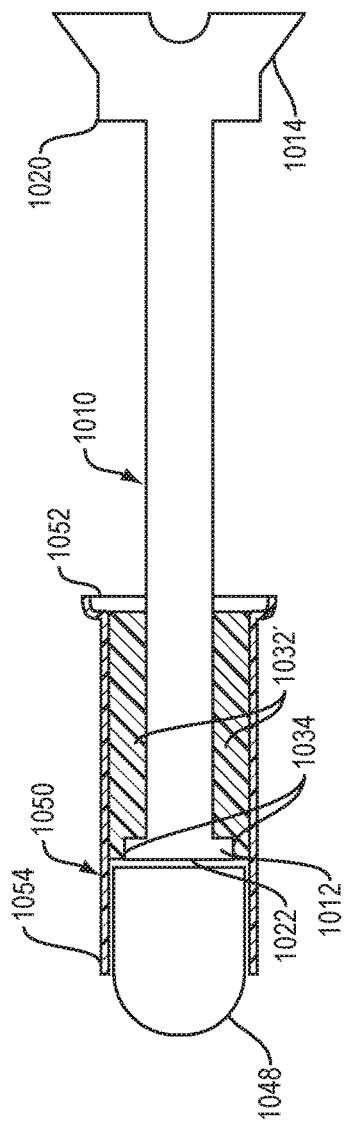
FIG. 10E is an illustration of an apparatus for inserting a suppository according to another example embodiment of the invention.

FIG. 10E is an illustration of an apparatus for inserting a suppository according to another example embodiment of the invention. This embodiment is similar to the apparatus shown in FIG. 10D, except that the one or more spacing elements 1032' are notched to let the insertion end 1012 of the body 1010 nest within the spacing elements. As shown, one or more spacing element(s) 1032' include respective notches 1034 configured to receive the insertion end 1012. The notches 1034 may be dimensioned such that the spacing elements 1032' and the suppository interface portion 1022 of the insertion end 1012 form a platform to support the suppository 1048. As described above, the wider diameter of the insertion end 1012 prevents the body 1010 from sliding away from the suppository 1048 and out of the gripping end 1054 of the outer element, e.g., barrel, 1050.

Figure 10F:
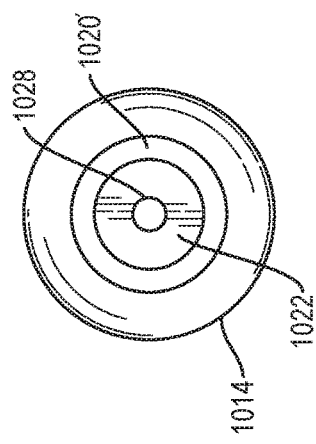
FIG. 10F is front view of an alternative embodiment of the invention.

FIG. 10F is front view of an alternative embodiment of the invention in which the stepped portion 1020' extends around the entire circumference of the body 1010 and the interface end 1014. As illustrated, the stepped portion 1020' can be circular, but it need not be. Also shown is the opening 1028 in the suppository interface portion 1022 of the insertion end 1012.

FIGS. 11A-11D are respective front, side, back, and sectional views of another example embodiment of an apparatus 1100 for inserting a suppository into an animal or human. Apparatus 1100 includes body 1110 having an insertion end 1112, a hand or finger-interface end 1114, and a central portion 1116 extending between the insertion end 1112 and the hand or finger interface-end 1114. The body 1110 can be substantially cylindrical and elongated. The insertion end 1112 has a larger diameter than the central portion 1116. The interface end 1114 includes an interface portion 1118 to interface with a hand or finger and a stepped portion 1120. As illustrated, the stepped portion 1120 is wider than the central portion 1116 and positioned between the central portion 1116 and the interface portion 1118. As shown in FIGS. 11A and 11B, the circular stepped portion 1120 extends around the circumference of the body 1110 and the interface end 1114. Further, the stepped portion 1120 defines four air pathways 1121 through the stepped portion. Air pathways 1121 ensure that any gas flow paths associated with the apparatus are not obstructed when the apparatus is used to insert a suppository.

FIG. 11D is a cross-section view of the apparatus 1100 along line A of FIG. 11B. As shown, the body 1110 of the apparatus defines a non-hollow structure, such as a solid rod or plunger, and may further define at least one spacing element 1130 extending outward from a wall 1111 of the structure 1110. The spacing element 1130 may be a gas flow path spacing element that extends outward from the wall 1111 of the structure. The spacing element 1130 may be configured to press on tissue between the anal canal or rectum and the apparatus in a manner defining at least one gas flow path.

Figure 12:
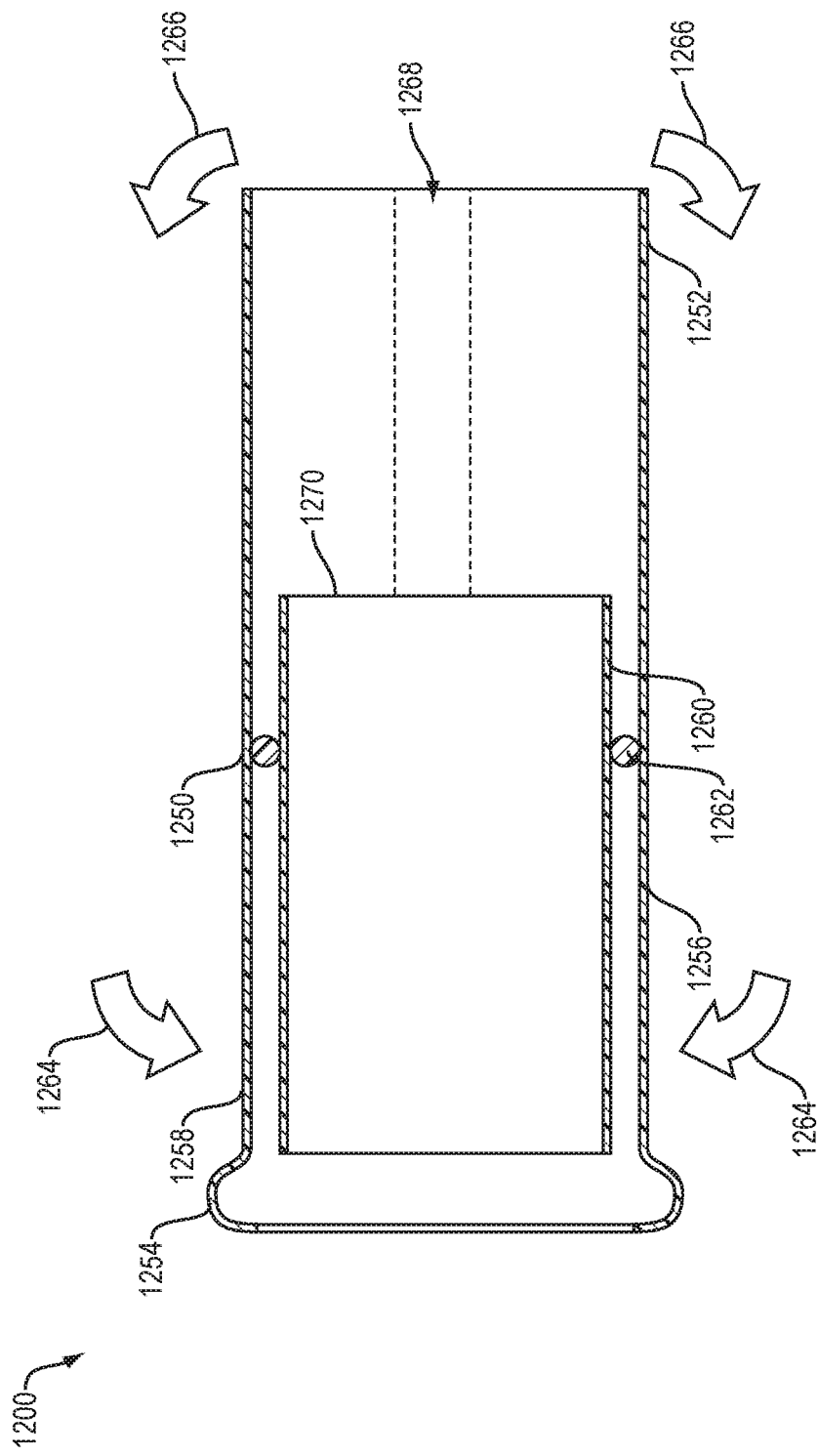
FIG. 12 is an illustration of an embodiment of the invention that can accommodate suppositories of various sizes.

FIG. 12 is an illustration of an alternative embodiment of the invention that can accommodate suppositories of various sizes. Apparatus 1200, which may be a barrel of an applicator for inserting a suppository into an animal or human, includes a hollow cylindrical body 1250 having an insertion end 1252, a gripping end 1254, and a central portion 1256. The central portion 1256 includes an outer wall 1258. An inner structure 1260 is coupled to the outer wall 1258 by an attachment 1262. The attachment 1262 may include one ore more attachment points, as illustrated, that allow the outer wall 1258 to move relative to the inner structure 1260 as the outer wall pivots about the one or more attachment points. The attachment 1262 may be integrally formed with the outer wall 1258, inner structure 1260, or both. In general, the body 1250 of the apparatus 1200 is mechanically arranged to enable squeezing (1264) of the central portion 1256 between the gripping end 1254 and the attachment 1262, whereby squeezing at the gripping end 1254 behind the attachment, e.g., between the gripping end 1254 and the attachment 1262, causes outward movement (1266) of the outer wall 1258 at the insertion end 1252 in front of the attachment. In this manner, the mechanical arrangement of apparatus 1200 can accommodate suppositories of different diameters. A user can use her fingers to squeeze or compress the central portion 1256 causing the outer wall 1258 at the insertion end 1252 to move outward, thereby enlarging the diameter of the insertion end to accommodate the diameter of the suppository to be inserted. As shown, the apparatus 1200 may further include a suppository support element 1270 configured to support a suppository at least partially inside the open insertion end 1252. In the example, a portion of the inner structure 1260 that faces the insertion end 1252 forms the support element 1270.

As part of the mechanical arrangement, the apparatus 1200 may include a longitudinal slot, cut, or opening 1268 in the outer wall 1258. Alternatively or in addition, the mechanical arrangement can include a portion of the outer wall that is structurally compliant enough to expand in response to squeezing 1264 of the central portion 1256. In addition, the compliant portion of the outer wall may expand in response to the insertion of a suppository into the insertion end 1252. To facilitate gripping of the apparatus 1200 by the user, the outer wall 1250 can include ridges (see, e.g., FIGS. 13A-13B). The ridges may extend from the gripping end 1254 along a length of the body. Furthermore, the gripping end 1254 has a larger diameter than the central portion 1256. The ridges and the wider diameter can improve the user's ability to grip the apparatus when loading a suppository into the insertion end 1252 or when using the apparatus, e.g., as a barrel in combination with a plunger element, to insert the suppository into an animal or human body, such as described above in reference to FIGS. 4A-4E. The ability to securely grip the apparatus when using the apparatus to insert a suppository into an anal canal or rectum is advantageous for self-administering the suppository, in particular in patients which suffer from reduced dexterity. Likewise, the cup-shaped finger-interface end 1014 of the plunger (see FIG. 10A-F) provides ease of use for such patients, and the insertion end 1012 of the plunger being wider than the inner structure 1270 ensures that the plunger does not inadvertently fall out of the apparatus, e.g., barrel, 1200 in an event of non-dexterous handling.

Figure 13A:
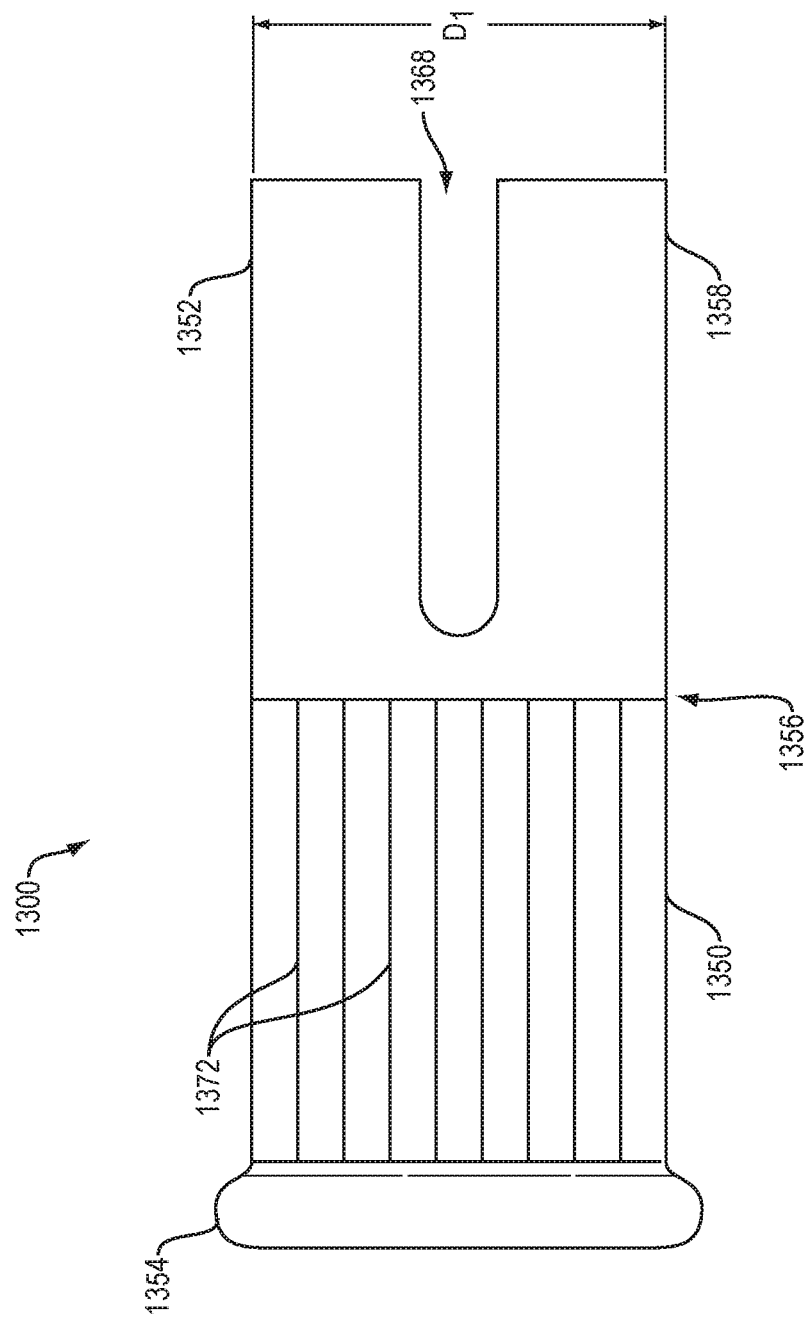

FIGS. 13A-13B are illustrations of another embodiment of the invention that can accommodate suppositories of various sizes. Apparatus 1300 for inserting a suppository into an animal or human includes a hollow cylindrical body 1350 having an insertion end 1352, a gripping end 1354, and a central portion 1356. The central portion 1356 includes an outer wall 1358. In the example embodiment shown, the outer wall 1358 includes ridges 1372 that extend from the gripping end 1354 along a length of the body 1350. Ridges may be formed by longitudinal grooves in the body 1350. Alternatively or in addition, ridges may be formed by longitudinal protrusions extending from the body 1350. The gripping end 1354 also has a larger diameter than the central portion 1356, including the portion of the body 1350 that includes the ridges. The larger diameter of the gripping end and the ridges are features facilitate handling of the apparatus and enable one-handed operation, which is advantageous during self-administration of a suppository.

As illustrated in FIG. 13B, the body 1350 of the apparatus 1300 is mechanically arranged to enable squeezing (1364) of the central portion 1356 at or near the gripping end 1354. Squeezing at the gripping end 1354, e.g., between the gripping end 1354 and a location along the length of the central portion 1356, causes outward movement (1366) of the outer wall 1358 at the insertion end 1352. In this manner, the mechanical arrangement can accommodate suppositories of different sizes (e.g., diameters). A user can use two fingers to squeeze the central portion 1356 causing the outer wall 1358 at the insertion end 1352 to move outward, thereby changing the diameter of the insertion end 1352 from a diameter $D_1$ (FIG. 13A) to a larger diameter in order to accommodate the diameter $D_2$ of the suppository 1348 to be inserted. As described in reference to embodiments of FIGS. 12 and 14, apparatus 1300 may include an inner structure that is coupled to the outer wall 1358 by one or more attachments. The apparatus 1300 may further include at least one suppository support element to support the suppository 1348 at least partially inside the open insertion end 1352 of the body 1350.

FIG. 14A-14C are illustrations of yet another embodiment of the invention that can accommodate suppositories of various sizes. The apparatus 1400 includes one or more spacers or spacing elements 1460a, 1460b (collectively 1460) that allow the body 1450 of the apparatus to flex open at the insertion end 1452 to receive a larger diameter suppository. One or more slots 1468 run along the length of the body 1450. As shown, the body 1450 is divided into two halves by two longitudinal slots 1468, the halves being held together by the spacer 1460. In the example shown, the spacer 1460 is placed midway in the body 1450 of the apparatus 1400.

FIG. 14B is a cross-sectional view of the central portion 1456 of the apparatus 1400 of FIG. 14A. The spacer 1460 can be thin, as illustrated, and may not be in contact with the entire inner circumference of the body 1450 to allow the body to flex open. As shown, each spacing element 1460a, 1460b is coupled to both halves of the body 1450 at contact points 1462. The spacing elements 1460a, 1460b are configured to define an area to receive a substantially cylindrical member, e.g., a plunger, and to maintain a gas flow path through the apparatus 1400, similar to flow path spacing elements described in reference to FIGS. 3 and 5.

FIG. 14C is a partial cut-away view of the apparatus 1400 of FIG. 14A. Shown is spacer 1460 positioned within the central portion 1456 between the insertion end 1452 and the gripping end 1454. Bumpers or nubs 1474 near the gripping end 1454 extend inward into the lumen of the body 1450. The apparatus 1400 and a plunger element can be assembled into an applicator for inserting a suppository. The bumpers 1474 can be configured to hit an outside wall of the plunger element, when positioned in the apparatus 1400, to limit the extent to which the outer wall 1458 of the central portion 1456 can be squeezed together at the gripping end 1454. In this manner, the bumpers 1474, in combination with a plunger (not shown), can stabilize to the apparatus 1400.

In any of the example embodiments described above, the apparatus may be formed from plastic, polycarbonate, epoxy, acrylic, silicone, rubber, polymer, ceramic, metal, cardboard, glass, wood, paper, or similar such materials.

While this invention has been particularly shown and described with references to example embodiments thereof, it will be understood by those skilled in the art that various changes in form and details may be made therein without departing from the scope of the invention encompassed by the appended claims. It should also be appreciated that the various technical features of the embodiments that have been described may be combined in various ways to produce numerous additional embodiments. For example, any plunger described herein may be provided with a hand or finger-interface end that includes a stepped portion or that includes notches or holes to provide a gas pathway.

What is claimed is:

1. An apparatus for inserting a suppository into an animal or human, the apparatus comprising:
a hollow cylindrical body having an insertion end, a gripping end, and a central portion between the insertion end and the gripping end, the central portion including an outer wall and an inner structure at a static location relative to the outer wall and coupled to the outer wall by an attachment, the inner structure having an axial length that is shorter than an overall length of the central portion, the body defining a mechanical arrangement that enables squeezing of the central portion between the gripping end and the attachment, with squeezing at the gripping end behind the attachment causing outward movement of the outer wall at the insertion end in front of the attachment.

2. The apparatus according to claim 1, wherein the mechanical arrangement includes a longitudinal slot in the outer wall.

3. The apparatus according to claim 1, wherein the mechanical arrangement includes a portion of the outer wall being structurally compliant enough to expand in response to insertion of a suppository into the insertion end.

4. The apparatus according to claim 1, wherein the mechanical arrangement is configured to accommodate suppositories of different diameters.

5. The apparatus according to claim 1, further including a suppository support element configured to support a suppository at least partially inside an open end of the body.

6. The apparatus according to claim 1, wherein the outer wall includes ridges that extend from the gripping end along a length of the body.

7. The apparatus according to claim 1, wherein the gripping end has a larger diameter than the central portion.

8. The apparatus according to claim 1, wherein the apparatus is formed from at least one of the following materials: plastic, polycarbonate, epoxy, acrylic, silicon, rubber, polymer, ceramic, metal, cardboard, glass, wood or paper.

9. The apparatus according to claim 1, wherein the attachment is integrally formed with the outer wall and inner structure of the central portion.

10. The apparatus according to claim 1, wherein the attachment includes one or more attachment points that allow the outer wall to move relative to the inner structure as the outer wall pivots about the one or more attachments points.

11. The apparatus according to claim 1, wherein the inner structure defines a cross-sectional area sized to have a plunger pass therethrough.

12. The apparatus according to claim 11, wherein the inner structure defines a suppository support structure configured to support a suppository.

13. The apparatus according to claim 11, wherein one or more spacing elements compose the inner structure and define a cross-sectional area configured to receive the plunger.

14. The apparatus according to claim 13, wherein the body is divided into two halves by two longitudinal slots, the halves being held together by the one or more spacing elements.

15. An apparatus for inserting a suppository into an animal or human, the apparatus comprising:
a hollow cylindrical body having an insertion end, a gripping end, and a central portion between the insertion end and the gripping end, the central portion including an outer wall and an inner structure at a static location relative to the outer wall and coupled to the outer wall by an attachment, the attachment being integrally formed with the outer wall and the inner structure of the central portion, the body defining a mechanical arrangement that enables squeezing of the central portion between the gripping end and the attachment, with squeezing at the gripping end behind the attachment causing outward movement of the outer wall at the insertion end in front of the attachment.

* * * * *